United States Patent [19]

Yoshikawa et al.

[11] Patent Number: 5,747,518
[45] Date of Patent: May 5, 1998

[54] SUBSTITUTED THIOPHENE DERIVATIVE AND AGRICULTURAL AND HORTICULTURAL FUNGICIDE CONTAINING THE SAME AS ACTIVE INGREDIENT

[75] Inventors: Yukihiro Yoshikawa; Kanji Tomiya; Hiroyuki Katsuta; Hideo Kawashima; Osamu Takahashi; Shunichi Inami; Yuji Yanase; Junro Kishi; Hitoshi Shimotori; Naofumi Tomura, all of Chiba-ken, Japan

[73] Assignee: Mitsui Toatsu Chemicals, Inc., Tokyo, Japan

[21] Appl. No.: 627,929

[22] Filed: Apr. 3, 1996

[30] Foreign Application Priority Data

Apr. 11, 1995 [JP] Japan ..................... 7-085601
Dec. 27, 1995 [JP] Japan ..................... 7-340480

[51] Int. Cl.$^6$ ............ A61K 31/415; A61K 31/425; A61K 31/38; A61K 31/44
[52] U.S. Cl. ............ 514/403; 514/370; 514/365; 514/444; 514/445; 514/447; 514/448; 514/336; 514/255; 548/365.7; 548/200; 548/194; 549/59; 549/60; 549/61; 549/62; 549/63; 549/66; 549/69; 549/70; 549/71; 549/72; 549/73; 546/280.4
[58] Field of Search ............ 548/365.7, 193, 548/194, 195, 198, 200; 549/69, 59, 60, 61, 63, 64, 66; 514/403, 447, 444, 445, 448, 365, 370, 336, 255; 546/280.4; 544/405, 406

[56] References Cited

U.S. PATENT DOCUMENTS

| | | |
|---|---|---|
| 3,823,161 | 7/1974 | Lesser .......................... 549/69 |
| 4,113,956 | 9/1978 | Moon et al. ..................... 548/374 |
| 4,240,820 | 12/1980 | Dickore et al. .................. 549/69 |
| 4,472,425 | 9/1984 | Sandmeier et al. ............... 549/69 |
| 4,500,536 | 2/1985 | Yosida et al. ................... 514/397 |
| 4,767,758 | 8/1988 | Breccia et al. .................. 514/231.5 |
| 5,039,694 | 8/1991 | Suzuki et al. ................... 514/406 |
| 5,073,184 | 12/1991 | Anthony et al. ................. 549/69 |
| 5,330,995 | 7/1994 | Eicken et al. ................... 514/355 |
| 5,438,070 | 8/1995 | Eicken et al. ................... 514/403 |
| 5,480,897 | 1/1996 | Eicken et al. ................... 514/365 |

FOREIGN PATENT DOCUMENTS

| | | |
|---|---|---|
| 545 099 | 11/1992 | European Pat. Off. . |
| 589 301 | 9/1993 | European Pat. Off. . |
| 639 574 | 8/1994 | European Pat. Off. . |

*Primary Examiner*—Richard L. Raymond
*Assistant Examiner*—Deborah Lambkin
*Attorney, Agent, or Firm*—Millen, White, Zelano, & Branigan, P.C.

[57] ABSTRACT

The substituted thiophene derivative of the invention which is represented by the general formula (1) has a broad disease spectrum for a pathogenic fungus of various crops, exhibits an excellent controlling effect on disease such as gray mold, powdery mildew and rust in particular, and is also effective for a resistant fungus of conventional fungicides which has become a serious problem, and consequently is useful for an agricultural and horticultural fungicide.

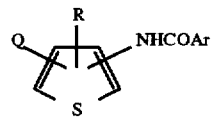

(1)

17 Claims, No Drawings

SUBSTITUTED THIOPHENE DERIVATIVE AND AGRICULTURAL AND HORTICULTURAL FUNGICIDE CONTAINING THE SAME AS ACTIVE INGREDIENT

BACKGROUND OF THE INVENTION

1) Field of the Invention

The present invention relates to a novel substituted thiophene derivative, an agricultural and horticultural fungicide containing the same as in active ingredient and a method for controlling plant disease by the same.

2) Description of Related Art

Recently developed fungicides having selective mechanism of action differ from conventionally used, nonselective fungicides for exhibiting steady effect at low dosage. However, the recent fungicides have a problem of developing chemical tolerance and leading to reduction of efficacy. For example, a benzimidazole fungicide has a broad fungicidal spectrum and exhibits excellent effect also on gray mold disease. However, such fungicide caused a drastic reduction of efficacy due to appearance of a resistant fungus against said fungicide in the 1970's. A dicarboxyimide fungicide was focused attention as a replacement of the benzimidazole fungicide. Nevertheless, a resistant fungus also appeared against the dicarboxyimide fungicide in the 1980's. Consequently, the lack of the counter measure for controlling the resistant fungus of gray mold disease has become a serious problem in Japan and also in the world.

On the other hand, an azole fungicide has a broad fungicidal spectrum and is an excellent pesticide which exhibits efficacy at a previously unknown low dosage particularly for powdery mildew disease and rust disease of various crops and scab disease of apple and pear. However, a resistant fungus against this fungicide has recently appeared and also led to a problem of a sharp fall of the fungicide efficacy. Such occurence of fungicide resistant fungus has become an inevitable problem for the selective fungicide, and accordingly development of a new fungicide is now an urgent subject.

Many aromatic aniline derivatives have conventionally been known to have fungicidal activity. For example, Japanese Laid-Open Patent Hei 5-221994 and 6-199803 have disclosed that various aniline derivatives have efficacy for gray mold disease. The present inventors have tested fungicidal activity against various plant-pathogenic fungi on the compounds disclosed in these patents. However, the disease control effect was low even in the case of gray mold disease and no efficacy was observed at all on powdery mildew disease and brown rust disease.

Consequently, the object of the invention is to provide a novel agricultural and horticultural fungicide which has a broad spectrum for pathogenic fungus of various crops and can also solve the resistant fungus which has become a serious problem.

SUMMARY OF THE INVENTION

As a result of an intensive research on the bioactivity of various heterocyclic amine derivatives, the present inventors have found that some kinds of aminothiophene derivative have powerful controlling effect on various plant disease and exhibit excellent controlling activity for not only a sensitive fungus but a resistant fungus of benzimidazole and dicarboxyimide fungicides, and further for the sensitive fungus and resistant fungus of an azole fungicide and that such aminothiophene derivative has high safety for crops and consequently can attain the above object. Thus the present invention has been completed.

That is, the aspect of the invention is a substituted thiophene derivative represented by the general formula (1), an agricultural and horticultural fungicide comprising the same as an active ingredient and a method for controlling plant disease by the same.

(1)

wherein Q is a hydrogen atom, fluorine atom, chlorine atom, bromine atom, iodine atom, methyl group, trifluoromethyl group, methoxy group, methylthio group, methylsulfonyl group, methylsulfoxy group, cyano group, acetyl group, nitro group, alkoxycarbonyl group or amino group; R is a straight or branched alkyl group having 1–12 carbon atoms, straight or branched halogenoalkyl group having 1–12 carbon atoms, straight or branched alkenyl group having 2–10 carbon atoms, straight or branched halogenoalkenyl group having 2–10 carbon atoms, alkoxyalkyl group having 2–12 carbon atoms, alkylthioalkyl group having 2–10 carbon atoms, cycloalkyl group having 3–10 carbon atoms, halogen substituted cycloalkyl group having 3–10 carbon atoms, or a phenyl group which can be substituted with 1–3 substituents; the substituent of said phenyl group is a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group or amino group substituted with alkyl group having 1–3 carbon atoms; R and the group —NHCOAr are adjacent to each other; and Ar is a group represented by (A1) to (A8) below:

(A1)

(A2)

(A3)

(A4)

3

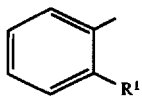
(A5)

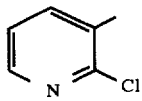
(A6)

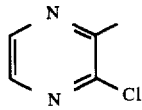
(A7)

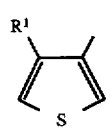
(A8)

wherein R¹ is a trifluoromethyl group, difluoromethyl group, methyl group, ethyl group, chlorine atom, bromine atom or iodine atom. R² is a hydrogen atom, methyl group, trifluoromethyl group or amino group, and n is an integer of 0–2.

Another aspect of the invention is intermediates of the substituted thiophene derivative represented by the general formula (1), that is, an aminothiophene derivative represented by the general formula (2):

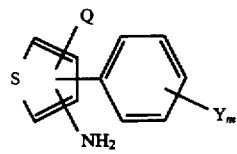
(2)

wherein Q is a hydrogen atom, fluorine atom, chlorine atom, bromine atom, iodine atom, methyl group, trifluoromethyl group, methoxy group, methylthio group, methylsulfonyl group, methylsulfoxy group, cyano group, acetyl group, nitro group, alkoxycarbonyl group or amino group; Y is a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, atkylthio group having 1–4 carbon atoms, alkylsulfoxy group having 1–4 carbon atoms, alkylsulfonyl group having 1–4 carbon atom, halogen atom, cyano group, acyl group having 2–4 carbon atoms, alkoxycarbonyl group having 2–4 carbon atoms, amino group or amino group substituted with alkyl group having 1–3 carbon atoms, m is an integer of 1–3, and a phenyl group and amino group are adjacent to each other; and a nitrothiophene derivative represented by the general formula (3)

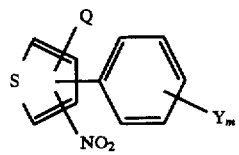
(3)

wherein Q is a hydrogen atom, fluorine atom, chlorine atom, bromine atom, iodine atom, methyl group, trifluoromethyl group, methoxy group, methylthio group, methylsulfonyl group, methylsufoxy group, cyano group, acetyl group, nitro group, alkoxycarbonyl group or amino group, Y is a hydrogen atom, alkyl group having 1–4 carbon atoms, alkenyl group having 2–4 carbon atoms, alkynyl group having 2–4

4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group or amino group substituted with alkyl group having 1–3 carbon atoms, m is an integer of 1–3, and a phenyl group and nitro group are adjacent to each other.

DETAILED DESCRIPTION OF THE INVENTION

Examples of the substituent R of the thiophene derivative represented by the general formula (1) in the invention specifically include isopropyl, sec-butyl, tert-butyl, 1-methylbutyl, 1-methylhexyl, 1-ethylpropyl, 1,2-dimethylbutyl, 1,3-dimethylbutyl, 1-ethyl-3-methylbutyl, 1,2-dimethylhexyl, 1,3-dimethyloctyl, 3-methylbutyl, 3-methylpentyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl, 1-methyl-2-cyclopropylethyl, n-butyl, n-hexyl and other straight or branched alkyl groups having 1–12 carbon atoms; 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl and other straight or branched halogenoalkyl groups having 1–12 carbon atoms; propenyl, 1-methyl-1-propenyl, 1-ethyl-1-butenyl, 2,4-dimethyl-1-pentenyl, 2,4-dimethyl-2-pentenyl and other straight or branched alkenyl groups having 2–10 carbon atoms; 2-chloro-1-methyl-1-butenyl and other halogenoalkenyl groups having 2–10 carbon atoms; cyclopropyl, cyclohexyl, 2-ethylcyclohexyl, 2-isopropylcyclohexyl and other cycloalkyl groups having 3–10 carbon atoms; methoxymethyl, 1-methoxyethyl, 1-ethoxyethyl, 1-methoxypropyl, 1-isopropoxyethyl and other alkoxyalkyl groups having 2–10 carbon atoms; methylthiomethyl, 1-methylthioethyl, 1-ethylthioethyl, 1-methylthiopropyl, 1-isopropylthioethyl and other alkylthioalkyl groups having 2–10 carbon atoms; 2-chlorocyclohexyl, 3-chlorocyclohexyl and other halogen substituted cycloalkyl groups having 3–10 carbon atoms; and phenyl groups which can be substituted with 1–3 substituents. Exemplary substituents of the phenyl group specifically include a hydrogen atom, methyl, ethyl, propyl, isopropyl, sec-butyl, tert-butyl and other alkyl groups having 1–4 carbon atoms; vinyl, isopropenyl, 1-methylpropenyl and other alkenyl groups having 2–4 carbon atoms; ethynyl, 1-propynyl and other alkynyl groups having 2–4 carbon atoms; cyclopropyl, cyclopentyl, cyclohexyl and other cycloalkyl groups having 3–6 carbon atoms; methoxy, ethoxy, butoxy and other alkoxy groups having 1–4 carbon atoms; trifluoromethoxy, 1,1,2,2,2-pentafluoroethoxy and other halogenoalkoxy groups having 1–4 carbon atoms; methylthio, ethylthio and other alkylthio groups having 1–4 carbon atoms; methylsulfoxy, butylsulfoxy and other alkylsulfoxy groups having 1–4 carbon atoms; methylsulfonyl, isopropylsulfonyl and other alkylsulfonyl groups having 1–4 carbon atoms; a halogen atom such as fluorine, chlorine, bromine and iodine, cyano group; acetyl, propionyl and other acyl groups having 2–4 carbon atoms; methoxycarbonyl, ethoxycarbonyl and other alkoxycarbonyl groups having 2–4 carbon atoms; an amino group; and dimethylamino, diethylamino, propylamino and other substituted amino groups having alkyl groups of 1–3 carbon atoms. The substituent R is preferably branched alkyl groups having 3–12 carbon atoms.

Exemplary Ar groups specifically include a 5-thiazolyl group wherein the 4-position is substituted with a trifluoromethyl, difluoromethyl, methyl or ethyl group, or a fluorine, chlorine, bromine or iodine atom, and the 2-position can be substituted with a methyl, trifluoromethyl or amino group, for example, 2-methyl-4-trifluoromethyl-5-thiazolyl, 2-methyl-4-difluoromethyl-5-thiazolyl, 2-methyl-4-chloro-5-thiazolyl, 2-methyl-4-iodo-5-thiazolyl, 4-trifluoromethyl-5-thiazolyl and 2,4-dimethyl-5-thiazolyl group; a 4-pyrazolyl group wherein the 3-position is substituted with a trifluoromethyl, difluoromethyl, methyl or ethyl group or a fluorine, chlorine, bromine or iodine atom and the 1-position is substituted with methyl group, for example, a 1-methyl-3-trifluoromethyl-4-pyrozolyl, 1-methyl-3-difluoromethyl-4-pyrazolyl, 1,3-dimethyl-4-pyrazolyl, 1-methyl-3-chloro-4-pyrazolyl, 1-methyl-3-bromo-4-pyrazolyl, and 1-methyl-3-iodo-4-pyrazolyl group; a 3-furyl group wherein the 2-position is substituted with a trifluoromethyl, difluoromethyl, methyl or ethyl group or a chlorine, bromine or iodine atom and the 5-position can be substituted with a methyl or trifluoromethyl group, for example, a 2-methyl-3-furyl and 2,5-dimethyl-3-furyl group; a 2-thienyl group wherein the 3-position is substituted with a trifluoromethyl, difluoromethyl, methyl or ethyl group or a chlorine, bromine or iodine atom and the 4- or 5-position can be substituted with a methyl group, for example, 3-methyl-2-thienyl, 3-chloro-2-thienyl, 3-iodo-2-thienyl, and 3,4-dimethyl-2-thienyl group; a phenyl group wherein the 2-position is substituted with a trifluoromethyl, difluoromethyl, methyl or ethyl group or a fluorine, chlorine, bromine or iodine atom; a 2-chloronicotinyl group; a 3-chloro-2-pyrazinyl group; and a 3-thienyl group wherein the 4-position is substituted with a trifluoromethyl, difluoromethyl, methyl or ethyl group or a chlorine, bromine or iodine atom, for example, a 4-methyl-3-thienyl and 4-chloro-3-thienyl group. Ar is preferably a 4-pyrazolyl group wherein the 3-position is substituted with a trifluoromethyl, difluoromethyl, methyl or ethyl group or a fluorine, chlorine, bromine or iodine atom and the 1-position is substituted with methyl group.

Q is preferably hydrogen atom.

The substituted thiophene derivative of the invention represented by the general formula (1) is a novel compound and can be prepared by the process according to the following reaction formula which is similar to a known process, that is, by reacting substituted aminothiophene with carboxylic halide represented by the general formula (5) in a molten state or in a solvent.

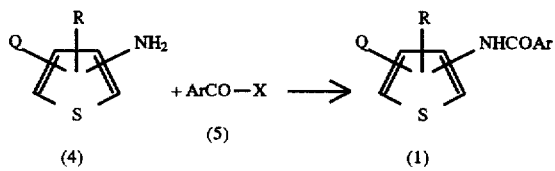

wherein Q, R and Ar are the same as above, X is a chlorine, bromine or iodine atom.

Any solvents which are inert in the reaction can be used for the reaction. Representative solvents include, for example, hexane, petroleum ether and other aliphatic hydrocarbons; benzene, toluene, chlorobenzene, anisole and other aromatic hydrocarbons; dioxane, tetrahydrofuran, diethyl ether and other ethers; acetonitrile, propionitrile and other nitrites; ethyl acetate and other esters; dichloromethane, chloroform, 1,2-dichloroethane and other halogenated hydrocarbons; and dimethylformamide, dimethyl sulfoxide and other aprotic solvents. These solvents can be used singly or as a mixture.

The reaction can also be carried out in the presence of a base. Exemplary bases include, for example, sodium hydroxide, potassium hydroxide, calcium hydroxide and other alkali metal and alkali earth metal hydroxides; calcium oxide, magnesium oxide and other alkali metal and alkali earth metal oxides; sodium hydride, calcium hydride and other alkali metal and alkali earth metal hydrides; lithium amide, sodium amide and other alkali metal amides; sodium carbonate, potassium carbonate, calcium carbonate, magnesium carbonate and other alkali metal and alkali earth metal carbonates; sodium hydrogen carbonate, potassium hydrogen carbonate and other alkali metal and alkali earth metal hydrogen carbonates; methyl lithium, butyl lithium, phenyl lithium, methyl magnesium and other alkali metal and alkali earth metal alkyls; sodium methoxide, sodium ethoxide, potassium, t-butoxide, dimethoxy magnesium and other alkali metal and alkali earth metal alkoxides; triethylamine, pyridine, N,N-dimethylaniline, N-methyl-piperidine, lutidine, 4-dimethylaminopyridine and other various organic bases. Triethylamine and pyridine are particularly preferred.

No particular limitation is imposed upon the amount of these bases. The amount used is preferably in excess of 5–20% by mole for the amount of carboxylic halide represented by the general formula (5).

In the above reaction, substituted aminothiophene represented by the general formula (4) and carboxylic halide represented by the general formula (5) are generally used in an amount of equal mole. In order to improve the yield, one material is sometimes used in excess of 1–20% by mole for the other material. The reaction temperature is usually −20°–150° C., preferably 0°–40° C.

No particular restriction is put upon the reaction time. The reaction time is commonly 30 minutes to 5 hours.

Next, the preparation process of the compounds represented by the general formula (4) which are intermediates of the invention will be illustrated.

1) Preparation of 2-substituted 3-aminothiophene (when the Substituent is not Phenyl Group)

The compounds are prepared, for example, by the process as shown by the following reaction formula wherein Ar has the above meaning, $R^3$ is a straight or branched alkyl group, halogenoalkyl, alkylthioalkyl, alkyloxyalkyl, cycloalkyl and halogen substituted cycloalkyl group, $R^4$ is a straight or branched alkyl group, alkylthioalkyl and cycloalkyl group and $R^5$ is an alkyl group. However, no restriction is imposed upon the preparation processes.

Method A

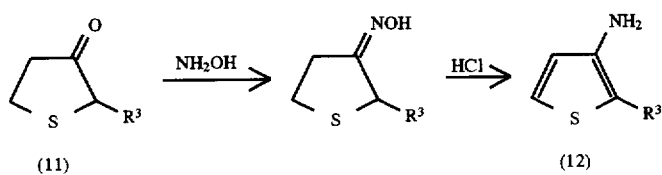

Method B-1

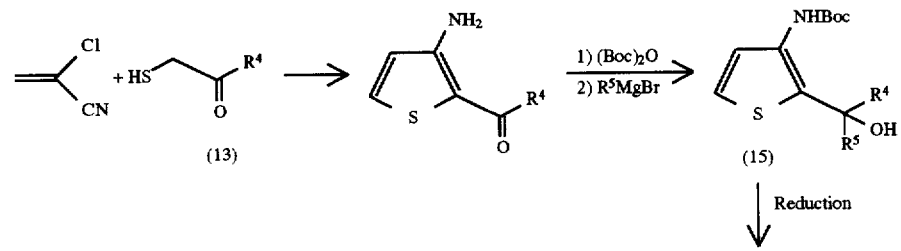

Method B-2

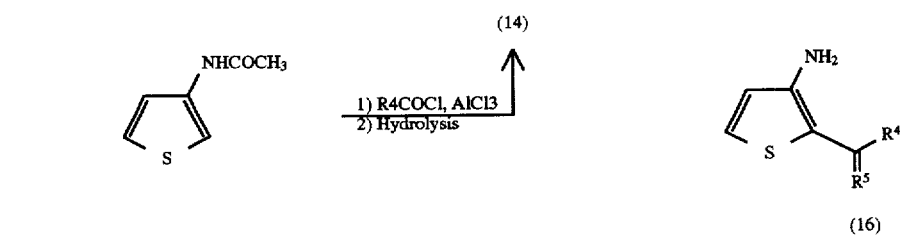

Method C

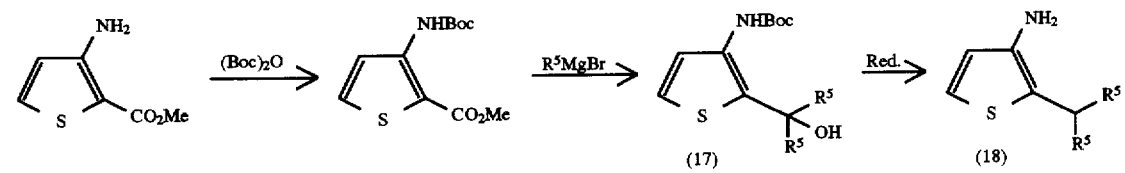

Method D

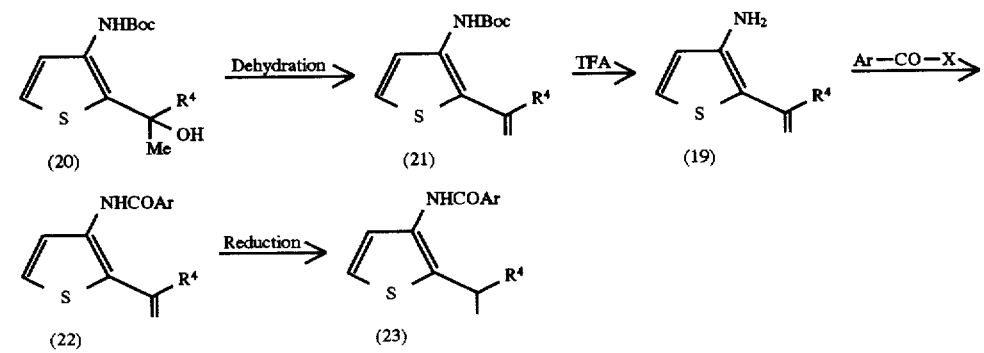

Process A is the process for converting 2-substituted 3-oxotetrahydrothiophene represented by the general formula (11) to oxime by reaction with hydroxylamine hydrochloride in ethanol in the presence of barium hydroxide and successively treating the oxime with hydrogen chloride in ethyl ether to obtain the amine represented by the general formula (12) [U.S. Pat. No. 4,317,915; J. Org. Chem.,52, 2611(1987)].

Process B-1 and B-2 is the process for preparing 2-acyl-3-aminothiophene represented by the general formula (14) by condensation of α-chloroarylonitrile with mercaptoacetone represented by the general formula (13) [Synth. Commun., 9, 731(1979)] or by acylation and hydrolysis of 3-acetylaminothiophene (Bull Soc. chim, Fr., 1976, 151) and for protecting thus obtained 2-acyl-3-aminothiophene with a t-butyloxycarbonyl group by using di-t-butylcarbonate in the presence of triethylamine, converting the protected aminothiophene to tertiary alcohol represented by the general formula (15) with an alkylating agent such as Grignard's reagent, and successively reducing the resultant tertiary alcohol to obtain the amine represented by the general formula (16).

Process C is the process for protecting 3-aminothiophene-2-carboxylate ester with a t-butyloxycarbonyl group by using di-t-butylcarbonate in the presence of triethylamine, converting the protected aminothiophene to tertiary alcohol represented by the general formula (17) with an alkylating agent such as Grignard's reagent, and successively reducing the resultant tertiary alcohol with triethylsilane in trifluoroacetic acid to obtain the amine represented by the general formula (18).

Process D is the process for dehydrating the compound represented by the general formula (20) with acetic anhydride and potassium bisulphate in dimethylformamide to the compound represented by the general formula (21) and successively releasing Boc group with trifluoroacetic acid to obtain the amine represented by the general formula (19).

Thus obtained 2-substituted 3-aminothiophene is used for preparation of the compound of the invention represented by the general formula (1). And 3-acylamino-2-alkylthiophene represented by the general formula (23) can be prepared by reducing directly 2-alkenyl-substitited 3-acylaminothiophene.

2) Preparation of 4-alkyl-3-aminothiophene

The compounds are prepared, for example, by the process as shown by the following reaction formula wherein $R^6$ is an alkyl group.

Method E

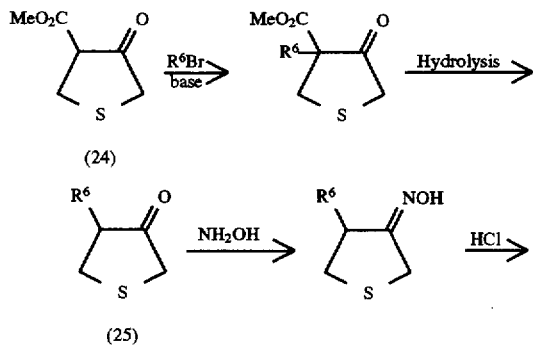

(24)

(25)

Method E
-continued

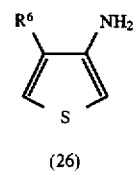

(26)

Process E is the process for alkylating 3-oxotetrahydrothiophene-4-carboxylate ester represented by the general formula (24) [U.S. Pat. No. 4,317,915 and J. Org. Chem.,52, 2611(1987)] with alkyl halide in the presence of potassium carbonate, hydrolyzing, decarboxylating to obtain 3-oxotetrahydrothiophene represented by the general formula (25), converting the resultant 3-oxotetrahydrothiophene to oxime with hydroxylamine-hydrochloric acid salt and barium hydroxide in ethanol and successively treating with hydrogen chloride in ethyl ether.

Thus obtained 4-alkyl-3-aminothiophene is used for preparation of the compound of the invention represented by the general formula (1).

Table 1 exemplifies 2-substituted 3-aminothiophene derivatives represented by the general formula (8). Table 2 exemplifies 4-alkyl-3-aminothiophene derivatives represented by the general formula (9).

TABLE 1

(2-substituted-3-aminothiophene derivatives)

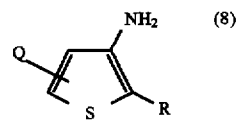

(8)

| R | Q | $^1$H-NMR(CDCl$_3$, δ-value, J:Hz) |
|---|---|---|
| isopropyl | H | 1.28(6H, d, J=7.3), 3.04(1H, sept, J=7.3), 3.07(2H, brs), 6.56(1H, d, J=5.9), 6.93(1H, d, J=5.9) |
| 1-methylpropyl | H | 0.92(3H, t, J=7.3), 1.25(3H, d, J= 7.3), 1.53–1.67(2H, m), 2.78(1H, sext, J=7.3), 3.35(2H, brs), 6.56( 1H, d, J=5.1), 6.95(1H, d, J=5.1) |
| (1S)-methylpropyl | H | 0.92(3H, t, J=7.3), 1.25(3H, d, J= 7.3), 1.53–1.67(2H, m), 2.78(1H, sext, J=7.3), 3.35(2H, brs), 6.56( 1H, d, J=5.1), 6.95(1H, d, J=5.1) |
| tert-butyl | H | |
| n-butyl | H | |
| 1-ethylpropyl | H | oil |

TABLE 1-continued (2-substituted-3-aminothiophene derivatives)

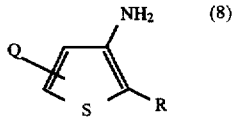 (8)

| R | Q | ¹H-NMR(CDCl₃, δ-value, J:Hz) |
|---|---|---|
| 1-methylbutyl | H | 0.90(3H, t, J=7.3), 1.25(3H, d, J=7.3), 1.28–1.40(2H, m), 1.52–1.63(2H, m), 2.87(1H, sext, J=7.3), 3.05(2H, brs), 6.55(1H, d, J=5.9), 6.95(1H, d, J=5.9) |
| n-hexyl | H | |
| 1,2-dimethylbutyl | H | 0.80–0.97(6H, m), 1.08–1.19(1H, m), 1.21–1.31(3H, m), 1.42–1.63(2H, m), 2.75(1H, quint, J=6.6), 3.32(2H, brs), 6.56(1H, d, J=5.1), 6.96(1H, d, J=5.1) |
| 1,3-dimethylbutyl | H | 0.89(3H, d, J=6.6), 0.90(3H, d, J=6.6), 1.23(3H, d, J=5.1)1.35–1.65(3H, m), 2.95(1H, sext, J=6.6), 3.35(2H, brs), 6.55(1H, d, J=5.1), 6.95(1H, d, J=5.1) |
| 1,3-dimethylbutyl | 5-Cl | |
| 1,3-dimethylbutyl | 5-Me | |
| 1,3-dimethylbutyl | 5-Br | |
| 1,3-dimethylbutyl | H | 0.81–0.86(6H, m), 1.21–1.27(8H, m), 3.05(1H, m), 3.35(2H, brs), 6.52(1H, d, J=5.2), 6.95(1H, d, J=5.2) |
| 1,3-dimethylhexyl | H | |
| 1,2-dimethylhexyl | H | |
| 1,3-dimethyloctyl | 5-Cl | |
| 3-methylbutyl | H | |
| 3-methylpentyl | H | |
| 4-methyloctyl | 5-Cl | |
| 1,2,2,3-tetramethylbutyl | H | |
| 1,3,3-trimethylbutyl | H | 0.84(9H, s), 1.26(3H, d, J=6.6), 1.56(2H, m), 3.08(1H, m), 3.40(2H, brs), 6.50(1H, d, J=5.7), 6.95(1H, d, J=5.7) |
| 1,2,3-trimethylbutyl | H | |
| 1,3-dimethylpentyl | 5-Me | |
| 1,3-dimethylhexyl | 5-Me | |
| 5-methyl-3-hexyl | H | |
| 2-methyl-4-heptyl | H | |
| 2,6-dimethyl-4-heptyl | H | |
| 1,4-dimethylpentyl | H | 0.83(6H, d, J=6.6), 1.12–1.64(8H, m) 2.91(1H, m), 3.05(2H, brs), 6.54(1H, d, J=4.9), 6.95(1H, d, J=4.9) |
| 1-methylpentyl | H | 0.85–0.92(3H, m), 1.24–1.33(6H, m), 1.53–1.59(3H, m), 2.83(1H, m), 3.34(2H, brs), 6.54(1H, d, J=4.9), 6.94(1H, d, J=4.9) |
| 1-methylhexyl | H | 0.84–0.86(3H, m), 3H, m), 1.23–1.29(11H, m) 2.94(1H, m), 3.32(2H, brs), 6.51(1H, d, J=5.1), 6.94(1H, d, J=5.1) |
| 1-methyl-2-cyclopropylethyl | H | oil |
| n-butyl | H | |
| 3-chloro-1-methylbutyl | H | |
| 2-chloro-1-methylbutyl | H | |
| 1-chlorobutyl | H | |
| 3,3-dichloro-1-methylbutyl | H | |
| 3-chloro-1-methylbutyl | H | |
| 1-methyl-3-trifluoromethylbutyl | H | |
| 3-methyl-1-trifluoromethylbutyl | H | |
| isopropenyl | H | oil |
| 1-methylthiopropyl | H | |
| 1-ethyl-1-butenyl | H | oil |

The terem "(1S)" means S-configuration at the 1-position and no description means a racemate.

TABLE 2

(4-substituted-3-aminothiophene derivatives)

$$\underset{S}{\overset{R \quad NH_2}{\underset{\diagdown}{\diagup}}} \quad (9)$$

| R | Q | Physical Properties |
|---|---|---|
| isopropyl | H | |
| sec-butyl | H | |
| tert-butyl | H | |
| 1-ethylpropyl | H | |
| 1-methylpropyl | H | |
| 1,2-dimethylbutyl | H | |
| 1,3-dimethylbutyl | H | |
| 1,3-dimethylbutyl | 5-Cl | |
| 1,3-dimethylbutyl | 5-Me | |
| 1,3,3-trimethylbutyl | H | |

3) Preparation of Aminothiophene wherein R can be a Substituted Phenyl Group

Any compounds represented by the above general formula (2) and general formula (3) are novel compounds and can be prepared by the process, for example, illustrated by the reaction formula below.

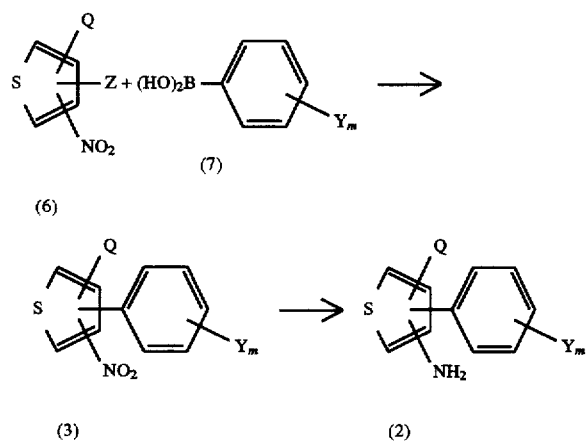

wherein Z is halogen atom, Q is a hydrogen, fluorine, chlorine, bromine or iodine atom or a methyl, trifluoromethyl, methoxy, methylthio, methylsulfonyl, cyano, acetyl, nitro, alkoxycarbonyl or amino group, Ym is a hydrogen or halogen atom or an alkyl having 1–4 carbon atoms, alkenyl having 2–4 carbon atoms, alkynyl having 2–4 carbon atoms, cycloalkyl having 3–6 carbon atoms, alkoxy having 1–4 carbon atoms, halogenoalkoxy having 1–4 carbon atoms, alkylthio having 1–4 carbon atoms, alkylsulfoxy having 1–4 carbon atoms, alkylsulfonyl having 1–4 carbon atoms, cyano, acyl having 2–4 carbon atoms, alkoxycarbonyl having 2–4 carbon atoms, amino or amino group substituted with an alkyl group having 1–3 carbon atoms, m is an integer of 1–3, and a phenyl group and amino group in the general formula (3) or a phenyl group and nitro group in the general formula (2) are adjacent to each other.

That is, the nitrothiophene derivative represented by the general formula (3) can be prepared by reacting halogenonitrothiophene of the general formula (6) with a phenylboric acid derivative of the general formula (7) in the presence of a Pd catalyst and base by way of a process similar to the processes reported in, for example, Synth. Commun., 11, 813(1981), Bull. Chem. Soc. Jpn., 61, 3008(1988), Chem. Lett., 1989, 1405, and J. Hetercycle. Chem. 28, 1613(1991). However, the processes are not limited to the specific embodiments.

Any solvents which are inert in the reaction can be used for the reaction. Representative solvents include, for example, hexane, petroleum ether and other aliphatic hydrocarbons; benzene, toluene, xylene, anisole and other aromatic hydrocarbons; dioxane, tetrahydrofuran, diethyl ether and other ethers; acetonitrile, propionitrile and other nitrites; ethyl acetate and other esters; dichloromethane, chloroform, 1,2-dichloroethane and other halogenated hydrocarbons; dimethylformamide, dimethyl sulfoxide and other aprotic solvents; methanol, ethanol and other alcohols; and water. These solvents can be used singly or as a mixture.

Exemplary bases include, for example, sodium hydroxide, potassium hydroxide, calcium hydroxide and other alkali metal and alkali earth metal hydroxides; calcium oxide, magnesium oxide and other alkali metal and alkali earth metal oxides; sodium hydride, calcium hydride and other alkali metal and alkali earth metal hydrides; lithium amide, sodium amide and other alkali metal amides; sodium carbonate, potassium carbonate, calcium carbonate, magnesium carbonate and other alkali metal and alkali earth metal carbonates; sodium hydrogen carbonate, potassium hydrogen carbonate and other alkali metal and alkali earth metal hydrogen carbonates; methyl lithium, butyl lithium, phenyl lithium, methyl magnesium and other alkali metal and alkali earth metal alkyls; sodium methoxide, sodium ethoxide, potassium, t-butoxide, dimethoxy magnesium and other alkali metal and alkali earth metal alkoxides; triethylamine, pyridine, N,N-dimethylaniline, N-methylpiperidine, lutidine, 4-dimethylaminopyridine and other various organic bases. Sodium carbonate and potassium carbonate are particularly preferred.

No particular limitation is imposed upon the amount of these bases. The amount used is preferably in 1.05–10 times and more preferably in 1.5–3 times by mole for the amount of halogenonitrothio phene represented by the general formula (5).

Exemplary Pd catalysts include $Pd(PPh_3)_4$, $PdCl_3$ and $Pd(OAc)_2$.

In the above reaction, halogenonitrothiophene represented by the general formula (6) and phenylboric acid derivative represented by the general formula (7) are generally used in an amount of equal mole. In order to improve the yield, one material is sometimes used in excess of 1–100% by mole for the other material. The reaction temperature is usually from room temperature to 150° C., preferably 80°–140° C.

No particular restriction is put upon the reaction time. The reaction time is commonly 30 minutes to 7 hours.

The aminothiophene derivative represented by the general formula (2) can be prepared, for example, by conducting catalytic reduction of a nitrothiophene derivative represented by the general formula (3) in methanol or ethanol in the presence of Pd/C catalyst or by reduction with Fe powder in acetic acid.

And a common method described in Shinjikkenkagaku Koza, 15, Oxidation and Reduction II [edited by Chem. Sec. Jpn, published from Maruzene Co. (1976)] can be also used for reduction of the nitrothiophene derivative represented by the general formula (2).

Table 3 exemplifies novel nitrothiophene derivatives represented by the general formula (3).

Table 4 exemplifies novel aminothiophene derivatives represented by the general formula (2).

TABLE 3

(phenyl-substituted nitrothiophene derivatives)

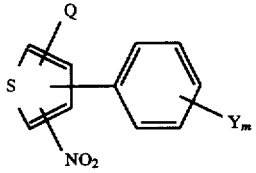

(3)

| Ym | Position of nitro group | Position of phenyl group | melting point (°C.) |
|---|---|---|---|
| H | 3- | 2- | 102–103 |
| 4-Cl | 3- | 2- | |
| 4-Me | 3- | 2- | |
| 4-OMe | 3- | 2- | 68–69 |
| 4-CF$_3$ | 3- | 2- | 67–69 |
| 3-Cl | 3- | 2- | 107–108 |
| 4-ter.-Bu | 3- | 2- | oil |
| 3,4-Cl$_2$ | 3- | 2- | 135–136 |
| 3,5-Cl$_2$ | 3- | 2- | 133–138 |
| 3-Me | 3- | 2- | 73–74 |
| 4-Br | 3- | 2- | 84–85 |
| 3-OMe | 3- | 2- | oil |
| 3-CF$_3$ | 3- | 2- | 53–54 |
| 4-SMe | 3- | 2- | 109–111 |
| 2-Cl | 3- | 2- | oil |
| 3,5-Me$_2$ | 3- | 2- | oil |
| 3-F | 3- | 2- | 80–83 |
| 3,4-F$_2$ | 3- | 2- | 114–116 |
| 2,4-Cl$_2$ | 3- | 2- | |
| 3-Cl-4-F | 3- | 2- | |
| 2,5-Cl$_2$ | 3- | 2- | |
| 4-Cl-3-CF$_3$ | 3- | 2- | |
| 4-Cl-3-Me | 3- | 2- | |
| 4-Cl | 3- | 2- | 108–110 |
| 4-Me | 3- | 2- | 93–94 |
| 4-OMe | 3- | 2- | 82–84 |

TABLE 4

(phenyl-substituted aminothiophene derivatives)

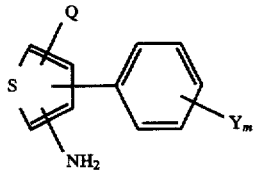

(2)

| Ym | Position of amino group | Position of phenyl group | M.P. (°C.) | $^1$H-NMR(CDCl$_3$, δ-value, J:Hz) |
|---|---|---|---|---|
| H | 3- | 2- | oil | 3.85(2H, brs), 6.66(1H, d, J=5.2), 7.10(1H, d, J=5.2), 7.25 (1H, m), 7.40(2H, m)7.52(2H, m) |
| H | 2- | 3- | * | |
| 4-Cl | 3- | 2- | 76–79 | 3.82(2H, brs), 6.64(1H, d, J=5.1), 7.12(1H, d, J=5.1), 7.34 –7.39(2H, m), 7.43–7.48(2H, m) |
| 4-Cl | 2- | 3- | * | |
| 4-Me | 3- | 2- | oil | 2.37(3H, s), 3.79(2H, brs), 6.54(1H, d, J=5.1), 7.09(1H, d, J=5.1), 7.22(2H, d, J=8.1), 7.41(2H, d, J=8.1) |
| 4-Me | 2- | 3- | * | |

TABLE 4-continued (phenyl-substituted aminothiophene derivatives)

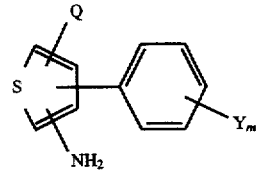

(2)

| Ym | Position of amino group | Position of phenyl group | M.P. (°C.) | $^1$H-NMR(CDCl$_3$, δ-value, J:Hz) |
|---|---|---|---|---|
| 3-Me | 3- | 2- | oil | 2.38(3H, s), 3.80(2H, brs), 6.65(1H, d, J=5.9), 7.06(1H, d, J=5.9), 7.06–7.08(1H, m), 7.10(1H, d, J=5.9), 7.30–7.33 (2H, m) |
| 4-OMe | 3- | 2- | oil | 3.77(2H, brs), 3.83(3H, s), 6.65(1H, d, J=5.9), 6.96(2H, d, J=8.8), 7.07(1H, d, J=5.9), 7.43(2H, d, J=8.8) |
| 4-OMe | 2- | 3- | * | |
| 4-CF$_3$ | 3- | 2- | oil | 4.00(2H, brs), 6.67(1H, d, J=5.1), 7.18(1H, d, J=5.1), 7.64 (4H, s) |
| 3-CF$_3$ | 3- | 2- | oil | 3.84(2H, brs), 6.67(1H, d, J=5.1), 7.17(1H, d, J=5.1, 7.45 –7.55(2H, m), 7.66–7.75(1H, m), 7.76(1H, s) |
| 3-Cl | 3- | 2- | oil | 3.84(2H, brs), 6.65(1H, d, J=5.1), 7.14(1H, d, J=5.1), 7.21 (1H, dd, J=8.8, 1.5), 7.35(1H, dt, J=8.8, 1.5), 7.41(1H, dd, J =8.8, 1.5), 7.51–7.53(1H, m) |
| 4-t-Bu | 3- | 2- | oil | 1.34(9H, s), 3.78(2H, brs), 6.65(1H, d, J=5.1), 7.09(1H, d, J=5.1), 7.40–7.47(4H, m) |
| 4-Et | 3- | 2- | oil | 1.25(3H, t, J=7.3), 2.67(2H, q, J=7.3), 3.60(2H, brs), 6.63 (1H, d, J=5.1), 7.09(1H, d, J=5.9), 7.24(2H, d, J=8.8), 7.42 (2H, d, J=8.8) |
| 4-Br | 3- | 2- | oil | 3.77(2H, brs), 6.65(1H, d, J=5.1), 7.13(1H, d, J=5.1), 7.37 –7.43(2H, m), 7.51–7.55(2H, m) |
| 4-I | 3- | 2- | oil | |
| 4-OCF$_3$ | 3- | 2- | oil | 3.85(2H, brs), 6.63(1H, d, J=5.1), 7.11(1H, d, J=5.1), 7.25 (2H, d, J=8.1), 7.52(2H, d, J=8.1) |
| 3-OMe | 3- | 2 | oil | 3.83(3H, s), 3.84(2H, brs), 6.64(1H, d, J=5.1), 6.80(1H, d, J=5.9), 7.05–7.12(3H, m), 7.31(1H, t, J=7.3) |
| 4-SMe | 3- | 2- | oil | 2.50(3H, t), 3.75(2H, brs), 6.65(1H, d, J=5.1), 7.10(1H, t, J=5.1), 7.29(2H, dd, J=8.1, 1.5), 7.44(2H, dd, J=8.1, 1.5) |
| 4-cyclo-propyl | 3- | 2- | oil | |
| 4-SO$_2$Me | 3- | 2- | oil | |
| 2-Cl | 3- | 2- | oil | 3.61(2H, brs), 6.66(1H, d, J=5.1), 7.20(1H, d, J=5.1), 7.26 –7.33(2H, m), 7.44–7.50(2H, m) |
| 2-Br | 3- | 2- | oil | |
| 4-F | 3- | 2- | oil | 3.74(2H, brs), 6.65(1H, d, J=5.9), 7.07–7.13(3H, m), 7.44–7.52(2H, m) |
| 3-F | 3- | 2- | | 3.84(2H, brs), 6.65(1H, d, J=5.9), 6.90–6.97(1H, m), 7.13( 1H, d, J=5.9), 7.20–7.40(3H, m) |

TABLE 4-continued (phenyl-substituted aminothiophene derivatives)

$$\text{structure (2)}$$

| Ym | Position of amino group | Position of phenyl group | M.P. (°C.) | $^1$H-NMR(CDCl$_3$, δ-value, J:Hz) |
|---|---|---|---|---|
| 2,4-Cl$_2$ | 3- | 2- | oil | 3.60(2H, brs), 6.65(1H, d, J=5.1), 7.22(1H, d, J=5.1), 7.28 (1H, dd, J=8.1, 2.2), 7.40(1H, d, J=8.1), 7.50(1H, d, J=2.2) |
| 3,4-Cl$_2$ | 3- | 2- | oil | 3.82(2H, brs), 6.64(1H, d, J=5.1), 7.15(1H, d, J=5.1), 7.35 (1H, dd, J=8.1, 2.2), 7.45(1H, d, J=8.1), 7.62(1H, d, J=2.2) |
| 3,5-Cl$_2$ | 3- | 2- | oil | 3.86(2H, brs), 6.64(1H, d, J=5.9), 7.16(1H, d, J=5.9), 7.22 (1H, t, J=1.5), 7.41(2H, d, J=1.5) |
| 3,4-F$_2$ | 3- | 2- | oil | 3.77(2H, brs), 6.64(1H, d, J=5.9), 7.12(1H, d, J=5.9), 7.15 –7.24(2H, m), 7.31–7.38(2H, m) |
| 3,5-Me$_2$ | 3- | 2- | oil | 2.35(6H, s), 3.79(2H, brs), 6.65(1H, d, J=5.1), 6.90(1H, s), 7.09(1H, d, J=5.1), 7.14(2H, s) |
| 3-F-4-Me | 3- | 2- | oil | 2.28(3H, d, J=1.4), 3.85(2H, brs), 6.62(1H, d, J=5.8), 7.09 (1H, d, J=5.8), 7.18(1H, d, J=8.1), 7.18(1H, s), 7.20(1H, d, J=8.1) |
| 4-F-3-Me | 3- | 2- | oil | 2.31(3H, s), 3.72(2H, brs), 6.62(1H, d, J=5.4), 7.03(1H, t, J=8.8), 7.09(1H, d, J=5.4) 7.25–7.32(2H, m) |
| 4-Cl-3-CF$_3$ | 3- | 2- | oil | 3.82(2H, brs), 6.64(1H, d, J=5.1), 7.16(1H, d, J=5.1), 7.52 (1H, d, J=8.8), 7.62(1H, dd, J=8.8, 2.2), 7.84(1H, d, J=2.2) |
| 4-Cl-3-F | 3- | 2- | oil | 3.83(2H, brs), 6.63(1H, d, J=5.1), 7.13(1H, d, J=5.1), 7.23 –7.43(3H, m) |
| 3-Cl-4-F | 3- | 2- | oil | 3.77(2H, brs), 6.64(1H, d, J=5.1), 7.06–7.21(2H, m), 7.32–7.40(1H, m), 7.56(1H, d, J=7.3) |
| 4-Cl-3-Me | 3- | 2- | oil | |
| 2-i-Pr | 3- | 2- | oil | |
| 3-OCF$_3$ | 3- | 2- | oil | |
| 2,5-Cl$_2$ | 3- | 2- | oil | |
| 2-Et | 3- | 2- | oil | |
| 2-Me | 3- | 2- | oil | 2.30(3H, s), 3.41(2H, brs), 6.66(1H, d, J=5.1), 7.14(1H, d, J=5.1), 7.19–7.34(4H, m) |
| 4-ethynyl | 3- | 2- | oil | |

*These compounds shown by "*" were unstable, so they were used for next reaction without separation from reaction solution of catalytic reduction.

The agricultural and horticultural fungicide which comprises the compound represented by the general formula (1) of the invention as an active ingredient has an excellent disease control effect on rice diseases such as Blast (*Pyricularia oryzae*), Helminthosporium leaf spot (*Cochliobolus miyabeanus*), Sheath blight (*Rhizoctonia solani*), "Bakanae" disease (*Gibberella fujikuroi*), Wheat Powdery mildew (*Erysiphe graminis* f.sp.*hordei*; f.sp.*tritici*), Leaf stripe (*Pyrenophora graminea*), Net blotch (*Pyrenophora teres*), Fusarium blight (*Gibberel la zeae*), Stripe rust (*Puccinia striiformis*, Stem rust (*P. graminis*), Brown rust (*P. recondita*), Brown rust (*P. hordei*), Snow rot (*Typhula* sp.; *Micronectriella nivalis*), Loose smut (*Ustilago tritici*; *U. nuda*), Eye spot (*Pseudocercosporella herpotrichoides*), Rhynchosporium leaf blotch (*Rhynchosporium secalis*), Septoria leaf blotch (*Septoria tritici*), Glume blotch (*Leptosphaeria nodorum*), Grape Powdery mildew (*Uncinula necator*), Anthracnose (*Elsinoe ampelina*), Ripe rot (*Glomerella cingulata*), Rust (*Phakopsora ampelopsidis*), Apple Powdery mildew (*Podosphaera leucotricha*), Scab (*Venturia inaequalis*), Alternaria leaf spot (*Alternaria mali*), Rust (*Gymnosporangium yamadae*), Blossom blight (*Sclerotinia mali*), Canker (*Valsa mali*), Pear Black spot (*Alternaria kikuchiana*), Scab (*Venturia nashicola*), Rust (*Gymnosporangium haraeanum*), Peach Brown rot (*Sclerotinia cinerea*), Scab (*Cladosporium carpophilum*), Phomopsis rot (*Phomopsis* sp.), Persimmon Anthracnose (*Gloeosporium kaki*), Angular leaf spot (*Cercospora kaki*; *Mycosphaerella nawae*), Melon Powdery mildew (*Sphaerotheca fuliginea*), Anthracnose (*Colletotri chum lagenarium*), Gummy stem blight (*Mycosphaerella melonis*), Tomato Early blight (*Alternaria solani*), leaf mold (*Cladosporium fulvam*), Eggplant Powdery mildew (*Erysiphe cichoracoarum*), Alternaria leaf spot (*Alternaria japonica*), White spot (*Cerocosporella barassicae*), Leak Rust (*Puccinia allii*), Beans Purple spec (*Cercospora kikuchii*), Sphaceloma scab (*Elsinoe glycines*), Pod and stem blight (*Diaporthe phaseololum*), Beans Anthracnose (*Colletotrichum lindemuthianum*), Leaf spot (*Mycosphaerella personatum*), Brown leaf spot (*Cercospora arachidicola*), Powdery mildew (*Erysiphe pisi*), Early blight (*Alternaria solani*), Net blister blight (*Exobasidium reticulatum*), White scab (*Elsinoe leucospila*), Brown spot (*Alternaria longipes*), Beans Powdery mildew (*Erysiphe cichoracearum*), Anthracnose (*Colletotrichum tabacum*), Cercospora leaf spot (*Cercospora beticola*), Black spot (*Diplocarpon rosae*), Powdery mildew (*Sphaerotheca pannosa*), Leaf blotch (*Septoria chrysanthemi-indici*), Rust (*Puccinia horiana*), Powdery mildew (*Sphaerotheca humuli*), Gray mold (*Botrytis cinerea*) and Sclerotinia rot (*Sclerotinia sclerotiorum*)

When the compound represented by the general formula (1) of the invention is used as an agricultural and horticultural fungicide, the technical compound can be applied as intact to the plant to be treated. However, the technical compound is generally mixed with an inert liquid carrier or solid carrier and used in the form of a dust formulation, wettable powder, flowable formulation, emulsifiable concentrate, granule and other commonly used formulations. Adjuvant can also be added when necessary in view of formulation.

The term "carrier" means a synthetic or natural, inorganic or organic material which is formulated in order to assist reach of the effective ingredient to the portion to be treated and also to make storage, transport and handling of the effective ingredient compound easy. Any solid or liquid material can be used for the carrier so long as the material is commonly used for agricultural and horticultural formulations. No particular restriction is imposed on the carrier.

Solid carriers which can be used include, for example, montmorillonite, kaolinite and other clays; diotomaceous earth, Chine clay, talc, vermiculite, gypsum, calcium carbonate, silica gel, ammonium sulfate and other inorganic materials; soy bean powder, saw dust, wheat powder and other plant organic materials and urea.

Exemplary liquid carriers include toluene, xylene, cumene and other aromatic hydrocarbons; kerosine, mineral oil and other paraffin hydrocarbons; acetone, methyl ethyl ketone and other ketones; dioxane, diethylene glycol dimethyl ether and other ethers; methanol, ethanol, propanol, ethylene glycol and other alcohols; dimethylformamide, dimethyl sulfoxide and other aprotic solvents; and water.

In order to further enhance the effect of the compound in the invention, following adjuvant can also be used singly or as a mixture depending upon the object in view of the formulation and application place.

Adjuvant which can be used include surfactants and binders which are commonly used for agricultural and horticultural formulations, for example, ligninsulfonic acid, alginic acid, polyvinyl alcohol, gum arabic and sodium CMC, and stabilizers, for example, phenol compounds, thiophenol compounds and higher fatty acid ester for oxidation inhibition, phosphoric acid salts for pH regulation and light stabilizers in some cases. These adjuvant can be used singly or in combination, when needed. Further, an industrial fungicide or a bacteria proofing agent can also be added in a certain case in order to inhibit fungus and bacteria.

The adjuvants will be illustrated further in detail.

Exemplary adjuvants which can be used for the purpose of emulsification, dispersion, spreading, wetting, binding and stabilization include salt of ligninsulfonic acid, salt of alkylbenzenesulfonic acid, ester salt of alkylsulfate, polyoxyalkyleneal kylsulfate, ester salt of polyoxyalkylenealkylphosphate and other anionic surface active agents; polyoxyalkylene alkyl ether, polyoxalkylene alkyl aryl ether, polyoxyalkylene alkylamine, polyoxyalkylene alkylamide, polyoxyalkylene alkyl thioether, polyoxyalkylene fatty acid ester, glycerin fatty acid ester, sorbitan fatty acid ester, polyoxyalkylenesorbitan fatty acid ester, polyoxypropylene-polyoxyethylene block copolymer and other nonionic surface active agents; calcium stearate, wax and other lubricants, isopropyl hydrogen phosphate and other stabilizers; and other miscellaneous materials such as methylcellulose, carboxymethylcellulose, casein and gum arabic. However, no restriction is imposed upon these adjuvants.

The content of the compound represented by the general formula (1) in the agricultural and horticultural fungicide of the invention differs depending upon formulation and is usually 0.05–20% by weight in the dust formulation, 0.1–80% by weight in the wettable powder, 0.1–20% by weight in the granule, 1–50% by weight in the emulsifiable concentrate, 1–50% by weight in the flowable formulation, and 1–80% by weight in the dry flowable formulation. Preferred concentration is 0.5–5% by weight in the dust formulation, 5–80% by weight in the wettable powder, 0.5–8% by weight in the granule, 5–20 by weight in the emulsifiable concentrate, 5–50 by weight in the flowable formulation and 5–50% by weight in the dry flowable formulation.

The content of adjuvants is 0–80% by weight and the content of the carrier is quantity obtained by subtracting the total content of the active ingredient compound and the adjuvants from 100% by weight.

The methods for applying the composition of the invention include seed disinfection and foliage application. However, the composition can exhibit satisfactory activity by any application method utilized by these who are skilled in the art.

Application amount and application concentration, are variant depending upon object crops, object diseases, abundance of disease damage, formulation of compound, application method and various environmental conditions. The amount of active ingredient is usually 50–1000 g/hectare, preferably 100–500 g/hectare in spraying. When a wettable powder, flowable formulation or emulsifiable concentrate is diluted with water and sprayed, the dilution is usually 200–20,000 times, preferably 1,000–5,000 times.

The agricultural and horticultural fungicide of the invention can of course be used in combination with other fungicides, insecticides, herbicides, plant-growth regulators and other agricultural chemicals; soil conditioners; or materials having fertilizer effect. A mixed formulation of the fungicide in the invention can also be prepared by using these materials.

Exemplary other fungicides include triadimefon, hexaconazole, prochloraz, triflumizole and other azole fungicides; metalaxyl, oxadixyl and other acyl alanine fungicides; thiophanate-methyl, benomil and other benzimidazole fungicides; manzeb and other dithiocarbamate fungicides; and TPN and sulphur.

Insecticides include, for example, fenitrothion, daiazinon, pyridafenthion, chlorpyrifos, marathon, phenthoate, dimethoate, methyl thiometon, prothiofos, DDVP, acephate, salithion, EPN and other organophosphate insecticides; NAC, MTMC, BPMC, pirimicarb, carbosulfan, methomyl and other carbamate insecticides; and ethofenprox, permethrin, fenvalerate and other pyrethroid insecticides. However, no restriction is imposed upon these materials.

EXAMPLES

The compound of the invention will be further specifically illustrated by way of examples.

Example 1

Preparation of N-[2-{3-(4-tolyl)}thienyl]-3-trifluoromethyl-1-methylpyrozole-4-carboxyamide
(Compound No. 3.9)

1) 2-nitro-3-(4-tolyl)thiophene

A mixture of 0.8 g of 3-bromo-2-nitrothiophene, 0.52 g of 4-tolylboric acid, 5 ml of a 2M-aqueous potassium carbonate solution, 2.5 ml of ethanol and 30 ml of toluene was stirred at room temperature for 30 minutes in a nitrogen atmosphere. Successively 0.15 g of Pd(PPh$_3$)$_4$ was added and refluxed by heating for 7 hours. After separating into two layers, the organic layer was washed with water and dried over anhydrous sodium sulfate. Solvent was distilled off under reduced pressure. The residue was purified by silica gel column chromatography to obtain 0.56 g (70% yield) of the product as a yellow crystal. $^1$H-NMR(CDCl$_3$, δ value):2.42(3H, s), 7.01(1H, d, J=5.1), 7.25(2H, d, J=8.1), 7.37(2H, d, J=8.1), 7.47(1H, d, J=5.1)

2) 2-amino-3-(4-tolyl)thiophene

After dissolving 0.5 g of 2-nitro-3-(4-tolyl)thiophene in 20 ml of dioxane, 0.25 g of 5% pd/C was added and catalytic reduction was carried out at room temperature for 5 hours. The solution obtained was filtered to recover the catalyst and the filtrate was used as intact for the next reaction.

3) N-[2-{3-(4-tolyl)}thienyl]-3-trifluoromethyl-1-methylpyrazole-4-carboxyamide

To the filtrate obtained in the above 2), 0.73 of pyridine and 0.45 of 3-trifluoromethyl-1-methylpyroazolecarbonyl chloride was added and stirred at room temperature for an hour. The reaction mixture was extracted with ethyl acetate, washed with an aqueous saturated sodium carbonate solution and dried over anhydrous sodium sulfate. Solvent was distilled off under the reduced pressure and the residue was purified by silica gel column chromatography to obtain 0.4 g of the desired product. The yield was 47% based on 2-nitro-3-(4-tolyl) thiophene.

Example 2

Preparation of N-[2-{3-(4-chlorophenyl)}thienyl]-3-trifluoromethyl-1-methylpyrazole-4-carboxyamide
(Compound No. 3.2)

1) 2-nitro-3-(4-chlorophenyl)thiophene

The same procedures as described in Example 1 were carried out except that 4-tolylboric acid was replaced by 4-chlorophenylboric acid. The yield was 91%. m.p.:108°–110° C. $^1$H-NMR(CDCl$_3$, δ value):7.00(1H, d, J=5.1), 7.37–7.44(4H, m),7.50(1H, d, J=5.1)

2) 2-amino-3-(4-chlorophenyl)thiophene

The same procedures as described in Example 1 were carried out except that 2-nitro-3-(4-tolyl)thiophene was replaced by 2-nitro-3-(4-chlorophenyl)thiophene, and the filtrate thus obtained was used as intact for the next reaction.

3) N-[2-{3-(4-chlorophenyl)}thienyl]-3-trifluoromethyl-1-methylpyrazole-4-carboxyamide The same procedures as described in Example 1 were carried out except that 2-amino-3-(4-tolyl)thiophene was replaced by 2-amino-3-(4-chlorophenyl)thiophene. The yield was 41% based on 2-nitro-3-(4-chlorophenyl)thiophene.

Example 3

Preparation of N-[3-{2-(4-chlorophenyl)}thienyl]-3-trifluoromethyl-1-methylpyrazole-4-carboxyamide
(Compound No. 1.61)

1) 3-nitro-2-(4-chlorophenyl)thiophene

To 50 ml of toluene, 1 g of 2-bromo-3-nitrothiophene, 0.75 g of 4-chlorophenylboric acid, 5 ml of a 2M-aqueous potassium carbonate solution and 2 ml of ethanol were added and stirred at room temperature for 30 minutes in a nitrogen atmosphere. Successively 0.28 g of Pd(PPh$_3$)$_4$ was added and heat-refluxed for 2 hours. The aqueous layer was separated from the reaction mixture and the organic layer was washed with water and dried over anhydrous sodium sulfate. The solvent was distilled off under reduced pressure and the residue thus obtained was purified by silica gel column chromatography to obtain 1.1 g of the product as a yellow crystal. The yield was 98%. $^1$H-NMR(CDCl$_3$, δ value):7.29(1H, d, J=5.9), 7.43(4H, s), 7.66(1H, d, J=5.9)

2) 3-amino-2-(4-chlorophenyl)thiophene

To 20 ml of acetic acid, 1 g of 3-nitro-2-(4-chlorophenyl)thiophene and 0.93 g of iron powder were added and heated for 2 hours at 60° C. The reaction mixture was filtered through a diatomaceous earth (Celite) layer. Ethyl acetate was added to the filtrate and extracted 5 times with a 5% aqueous hydrogen chloride solution. The aqueous layer was neutralized with sodium hydrogen carbonate and extracted with ethyl acetate. The organic layer was dried over anhydrous sodium sulfate. The solvent was distilled off under reduced pressure to obtain 0.54 g of the product as an yellow brown crystal. The yield was 62%. $^1$H-NMR(CDCl$_3$, δ value):3.82(2H, brs), 6.64(1H, d, J=5.1), 7.12(1H, d, J=5.1), 7.34–7.39(2H, m), 7.43–7.48(2H, m)

3) N-[3-{2-(4-chlorophenyl)}thienyl]-3-trifluoromethyl-1-methylpyrazole-4-carboxyamide To a solution containing 0.25 g of 3-amino-2-(4-chlorophenyl) thiophene and 0.38 g of pyridine in 20 ml of methylene chloride, a solution containing 0.3 g of 3-trifluoromethyl-1-methylpyrazole-4-carbonyl chloride in 5 ml of methylene chloride was dropwise added with stirring and reacted with stirring at room temperature for an hour. After finishing the reaction, the reaction mixture was successively washed with a 5% aqueous hydrochloric acid solution, saturated sodium hydrogen carbonate solution, saturated sodium chloride solution, and dried over anhydrous sodium sulfate. The solvent was distilled off under reduced pressure and the residue was purified by silica gel column chromatography to obtain 0.37 g of the desired product as a colorless crystal. The yield was 81%.

Example 4

Preparation of N-[3-{2-(4-tolyl)}thienyl]-3-trifluoromethyl-1-methylpyrazole-4-carboxyamide
(Compound No. 1.68)

1) 3-nitro-2-(4-tolyl)thiophene

The same procedures as described in Example 3 were carried out except that 4-chlorophenylboric acid was replaced by 4-tolylboric acid. The yield was 78%. $^1$H-NMR (CDCl$_3$, δ value):2. 41(3H, s), 7.23–7.27(3H, m), 7.37(2H, dd, J=2.2, 8.1) 7.64(1H, d, J=5.9)

2) 3-amino-2-(4-tolyl)thiophene

The same procedures as described in Example 3 were carried out except that 3-nitro-2-(4-chlorophenyl)thiophene was replaced by 3-nitro-2-(4-tolyl)thiophene. The yield was 68%. $^1$H-NMR(CDCl$_3$, δ value):2.37(3H, s), 3.79(2H, brs), 6.54(d, J=5.1), 7.09(1H, d, J=5.1), 7.22(2H, d, J=8.1), 7.41 (2H, d, J=8.1)

3) N-[3-{2-(4-tolyl)}thienyl]-3-trifluoromethyl-1-methylpyrazole-4-carboxyamide

The same procedures as described in Example 3 were carried out except that 3-amino-(4-chlorophenyl)thiophene was replaced by 3-amino-(4-tolyl)thiophene. The yield was 85%.

Example 5

Preparation of N-[3-{2-(4-methoxyphenyl)}thienyl]-3-trifluoromethyl-1-methylpyrazole-4-carboxyamide
(Compound No. 1.64)

1) 3-nitro-2-(4-methoxyphenyl)thiophene

The same procedures as described in Example 3 were carried out except that 4-chlorophenylboric acid was replaced by 4-methoxyphenylboric acid. The yield was 96%. $^1$H-NMR(CDCl$_3$, δ value):3.86(3H, s), 6.96(2H, d, J=7.3), 7.20(1H, d, J=5.1), 7.44(2H, d, J=7.3), 7.63(1H, d, J=5.1)

2) 3-amino-2-(4-methoxyphenyl)thiophene

The same procedures as described in Example 3 were carried out except that 3-nitro-2-(4-chlorophenyl)thiophene was replaced by 3-nitro-2-(4-methoxyphenyl)thiophene. The yield was 79%. $^1$H-NMR(CDCl$_3$, δ value):3.77(2H, brs), 3.83(3H, s), 6.65(1H, d, J=5.9), 6.96(2H, d, J=8.8), 7.07(1H, d, J=5.9), 7.43(2H, d, J=8.8)

3) N-[3-{2-(4-methoxyphenyl)}thienyl]-3-trifluoromethyl-1-methylpyrazole-4-carboxyamide The same procedures as described in Example 3 were carried out except that 3-amino-(4-chlorophenyl)thiophene was replaced by 3-amino-2-(4-methoxyphenyl)thiophene. The yield was 75%.

Example 6

Preparation of N-(2-isopropenyl-3-thienyl)-3-trifluoromethyl-1-methylpyrazole-4-carboxamide
(Compound No. 1.71)

1) Methyl 3-(t-butoxycarbonylamino)thiophene-2-carboxylate

To a solution containing 10 g of methyl 3-aminothiophene-2-carboxylate and 7.72 g of triethylamine in 50 ml of methylene chloride, a solution containing 13.9 g of di-t-butyl dicarbonate in 20 ml of methylene chloride was dropwise added and successively, a catalytic amount of 4-dimethylaminopyridine was added. The mixture was stirring at room temperature for 5 hours. After finishing the reaction, the organic layer was separated washed with water and dried over anhydrous sodium sulfate. The solvent was distilled off under reduced pressure and the precipitated crystal was filtered. The filtrate was purified by silica gel column chromatography to obtain 4.2 g of the product as a colorless crystal. The yield was 75%. $^1$H-NMR(CDCl$_3$, δ value):1.52(9H, s), 3.88(3H, s), 7.43(1H, d, J=5.1), 7.88(1H, d, J=5.1), 9.35(1H, brs)

2) 2-(1-hydroxy-1-methyl)ethyl-3-(t-butoxycarbonylamino)thiophene

In a nitrogen atmosphere, 6.5 ml of a 3M-ether solution of MeMgBr was diluted with 5 ml of THF and cooled to 10° C. A solution containing 1 g of methyl 3-(t-butoxycarbonylamino)-thiophene-2-carboxylate in 5 ml of THF was dropwise added to the above solution. The mixture was stirred at room temperature for 3 hours, successively poured into an aqueous ammonium chloride solution and extracted with ethyl acetate. The organic layer was washed with an aqueous saturated sodium chloride solution and dried over anhydrous sodium sulfate. The solvent was distilled off under reduced pressure to obtain the product as yellow oil. The yield was theoretical. $^1$H-NMR(CDCl$_3$, δ value):1.50(9H, s), 1.65(6H, s), 7.02(1H, d, J=5.1), 7.27(1H, d, J=5.1), 8.09(1H, brs)

3) 3-t-butoxycarbonylamino-2-isopropenylthiophene

To 10 ml of DMF, 1.8 g of 2-(1-hydroxy-1-methyl)ethyl-3-(t-butoxycarbonylamino)thiophene, 1.4 g of acetic anhydride and 0.06 g of potassium hydrogen sulfate were added and heated at 60° C. for 2 hours. Water was added to the reaction mixture and extracted with ethyl acetate. The organic layer was washed with an aqueous saturated sodium chloride solution and dried over anhydrous sodium sulfate. The solvent was distilled off under reduced pressure. The residue was purified by silica gel column chromatography to obtain 1.04 g of the product as orange oil. The yield was 60%. $^1$H-NMR(CDCl$_3$, δ value):1.50(9H, s), 2.11(3H, s), 5.18((1H, s), 5.27(1H, m), 6.71(1H, brs), 7.13(1H, d, J=5.9), 7.56(1H, d, J=5.9)

4) 3-amino-2-isopropenylthiophene hydrochloride

A solution containing 0.3 g of 3-(t-butoxycarbonylamino)-2-isopropenylthiophene in 7 ml of methylene chloride was cooled to 0° C., and 3 ml of a 4N-hydrogen chloride dioxane solution was added. The mixture obtained was used as intact for the next reaction.

5) N-(2-isopropenyl-3-thienyl)-3-trifluoromethyl-1-methylpyrazole-4-carboxamide

The above solution was cooled to 0° C. and 5 ml of pyridine was added. A solution containing 0.27 g of 3-trifluoromethyl-1-methylpyrazole-4-carbonyl chloride in 5 ml of methylene chloride was dropwise added to the above mixture and stirred at room temperature for an hour. The reaction mixture was washed successively with a 5% aqueous hydrochloric acid solution, saturated sodium hydrogen carbonate solution, aqueous saturated sodium chloride solution, and dried over anhydrous sodium sulfate. The solvent was distilled off under reduced pressure and the residue was purified by silica gel column chromatography to obtain 0.12 g of the desired product as a crystal. The yield was 30%.

Example 7

Preparation of N-[3-{2-(4-trifluoromethylphenyl)}thienyl]-3-trifluoromethyl-1-methylpyrazole-4-carboxamide (Compound No. 1.77)

1) 3-nitro-2-(4-trifluoromethylphenyl)thiophene

The same procedures as described in Example 3 were carried out except that 4-chlorophenylboric acid was replaced by 4-trifluoromethylboric acid. The yield was theoretical. $^1$H-NMR(CDCl$_3$, δ value):7.35(1H, d, J=5.9), 7.61 (2H, d, J=8.1), 7.69–7.76 (3H, m)

2) 3-amino-2-(4-trifluoromethylphenyl)thiophene

The same procedures as described in Example 3 were carried out except that 3-nitro-2-(4-chlorophenyl)thiophene was replaced by 3-nitro-2-(4-trifluoromethylphenyl)thiophene. The yield was 70%. $^1$H-NMR(CDCl$_3$, δ value):4.00(2H, brs), 6.67($^1$H, d, J=5.1), 7.18(1H, d, J=5.1), 7.64 (1H, s)

3) N-[3-{2-(4-trifluoromethylphenyl)}thienyl]-3-trifluoromethyl-1-methylpyrazole-4-carboxamide The same procedures as described in Example 3 were carried out except that 3-amino-(4-chlorophenyl)thiophene was replaced by 3-amino-2-(4-trifluoromethylphenyl)thiophene. The yield was 58%.

Example 8

Preparation of N-[3-{2-(3-chlorophenyl}thienyl]-3-trifluoromethyl-1-methylpyrazole-4-carboxamide (Compound No. 1.75)

1) 3-nitro-2-(3-chlorophenyl)thiophene

The same procedures as described in Example 3 were carried out except that 4-chlorophenylboric acid was replaced by 3-chlorophenylboric acid. The yield was 84%. $^1$H-NMR(CDCl$_3$, δ value):7.31(1H, d, J=5.9), 7.36–7.46 (3H, m), 7.48(1H, s), 7.66(1H, d, J=5.9)

2) 3-amino-2-(3-chlorophenyl)thiophene

The same procedures as described in Example 3 were carried out except that 3-nitro-2-(4-chlorophenyl)thiophene was replaced by 3-nitro-2-(3-chlorophenyl)thiophene. The yield was 71%. $^1$H-NMR(CDCl$_3$, δ value):3.84(2H, brs), 6.65(1H, d, J=5.1), 7.14(1H, d, J=5.1), 7.21(1H, dd, J=1.5, 8.8), 7.35(1H, dt, J=1.5, 8.8), 7.41(1H, dd, J=1.5, 8.8), 7.51–7.53(1H, m)

3) N-[3-{2-(3-chlorophenyl)}thienyl]-3-trifluoromethyl-1-methylpyrazole-4-carboxamide The same procedures as described in Example 3 were carried out except that 3-amino-(4-chlorophenyl)thiophene was replaced by 3-amino-2-(3-chlorophenyl)thiophene. The yield was 79%.

Example 9

Preparation of N-[3-(2-phenyl)thienyl]-4-trifluoromethyl-2-methylthiazole-5-carboxamide (Compound No. 1.62)

1) 3-nitro-2-phenylthiophene

The same procedures as described in Example 3 were carried out except that 4-chlorophenylboric acid was replaced by phenylboric acid. The yield was 85%. $^1$H-NMR (CDCl$_3$, δ value):7.27(1H, d, J=5.1), 7.42–7.51(5H, m), 7.65(1H, d, J=5.1)

2) 3-amino-2-phenylthiophene

The same procedures as described in Example 3 were carried out except that 3-nitro-2-(4-chlorophenyl)thiophene was replaced by 3-nitro-2-phenylthiophene. The yield was 81%. $^1$H-NMR(CDCl$_3$, δ value):3.82(2H, brs), 6.66(1H, d, J=5.1), 7.12(1H, d, J=5.1), 7.22–7.29(1H, m), 7.42(2H, dt, J=1.5, 7.3), 7.52(2H, dd, J=1.5, 7.3)

3) N-[3-(2-phenyl)thienyl]-4-trifluoromethyl-2-methylthiazole-5-carboxamide

To a solution containing 0.5 g of 3-amino-2-phenylthiophene and 0.70 g of pyridine in 30 ml of methylene chloride, a solution containing 0.79 g of 4-trifluoromethyl-2-methylthiazole-5-carbonyl chloride in 10 ml of methylene chloride was dropwise added with stirring and further stirred at room temperature for 1.5 hours. After finishing the reaction, the reaction mixture was successively washed with a 5% aqueous hydrochloric acid solution, saturated aqueous sodium hydrogen carbonate solution, and saturated aqueous sodium chloride solution, and thereafter dried over anhydrous sodium sulfate. The solvent was distilled off under reduced pressure. The residue was purified by silica gel column chromatography to obtain 0.59 g of the desired product as a colorless crystal. The yield was 51%.

Example 10

Preparation of N-[3-(2-phenyl)thienyl]-3-trifluoromethyl-1-methylpyrazole-4-carboxamide (Compound No. 1.60)

To a solution containing 0.2 g of 3-amino-2-phenylthiophene and 0.35 g of pyridine in 20 ml of methylene chloride, a solution containing 0.29 g of 3-trifluoromethyl-1-methylpyrazole-4-carbonyl chloride in 5 ml of methylene chloride was dropwise added with stirring and further stirred at room temperature for 2 hours. The reaction mixture was successively washed with a 5% aqueous hydrocloric acid solution, saturated aqueous sodium hydrogen carbonate solution and saturated aqueous sodium chloride solution, and thereafter dried over anhydrous sodium sulfate. The solvent was distilled off under reduced pressure and the residue was purified by silica gel column chromatography to obtain 0.28 g of the desired product as a colorless crystal. The yield was 66%.

Example 11

Preparation of N-[3-(2-phenyl)thienyl]-2-chlorobenzamide (Compound No. 1.96)

To a solution containing 0.18 g of 3-amino-2-phenylthiophene and 0.35 g of pyridine in 20 ml of methylene chloride, a solution containing 0.18 g of 2-chlorobenzoyl chloride in 5 ml of methylene chloride was dropwise added with stirring and further stirred at room temperature for an hour. The reaction mixture was successively washed with a 5% aqueous hydrogen chloride solution, saturated aqueous sodium hydrogen carbonate solution and saturated aqueous sodium chloride solution, and thereafter dried over anhydrous sodium sulfate. The solvent was distilled off under reduced pressure and the residue was purified by silica gel column chromatography to obtain 0.14 g of the desired product as a colorless crystal. The yield was 47%.

Example 12

Preparation of N-[3-(2-phenyl)thienyl]-2-chloronicotinamide (Compound No. 1.97)

To a solution containing 0.2 g of 3-amino-2-phenylthiophene and 0.35 g of pyridine in 20 ml of methylene chloride, a solution containing 0.20 g of 2-chloronicotinoyl chloride in 5 ml of methylene chloride was dropwise added with stirring and further stirred at room temperature for an hour. The reaction mixture was successively washed with a 5% aqueous hydrochloric acid solution, saturated aqueous sodium hydrogen carbonate solution and saturated aqueous sodium chloride solution, and thereafter dried over anhydrous sodium sulfate. The solvent was distilled off under reduced pressure and the residue was purified by silica gel column chromatography to obtain 0.11 g of the desired product as a colorless crystal. The yield was 39%.

Example 13

Preparation of N-[2-{(1S)-1-methylpropyl}-3-thienyl]-3-trifluoromethyl-1-methylpyrazole-4-carboxamide (Compound No. 1.2)

1) 3-amino-2-{(1S)-1-methylpropyl}thiophene (Process A)

In 50 ml of ethanol, 1.7 g of 2-{(1S)-1-methylpropyl}tetrahydrothiophene-3-one and 1.1 g of hydroxylamine hydrochloride were dissolved and 3.4 g of barium hydroxide·8 hydrate was added. The mixture was heat-refluxed for 3.5 hours. The reaction mixture was cooled and filtered to remove solid material. The solvent was distilled off from the filtrate under reduced pressure. The residue was dissolved in ethyl ether, washed with water and dried over anhydrous sodium sulfate. The solvent was distilled off under reduced pressure to obtain oxime compound. The oxime compound was dissolved in 50 ml of ethyl ether, 1.7 ml of a 6.5N-hydrogen chloride solution in methanol was added, and the mixture was stirred at room temperature for 3 hours. The reaction mixture was thereafter allowed to stand for 12 hours at the room temperature, neutralized with a saturated aqueous sodium hydrogen carbonate solution and extracted with ethyl ether. the ethyl ether layer was washed with a saturated aqueous sodium chloride solution and dried over anhydrous sodium sulfate. The solvent was distilled off under reduced pressure and the residue was purified by silica gel column chromatography to obtain 0.44 g of the product as yellow-oil. The yield was 26%.

2) N-[2-{(1S)-1-methylpropyl}-3-thienyl]-3-trifluoromethyl-1-methylpyrazole-4-carboxamide The same procedures as described in Example 3 were carried out except that 3-amino-2-(4-chlorophenyl)thiophene was replaced by 3-amino-2-{(1S)-1-methylpropyl}thiophene. The yield was 75%.

Example 14

Preparation of N-{2-(1,3-dimethylbutyl)-3-thienyl}-3-trifluoromethyl-1-methylpyrazole-4-carboxamide (Compound No. 1.13)

1) 2-(1-hydroxy-1,3-dimethylbutyl)-3-t-butoxycarbonylaminothiophene (Process B)

A tetrahydrofuran solution of 2-methylpropylmagnesiumbromide prepared from 2.9 g of 2-methylpropylbromide, 0.47 g of magnesium and 20 ml of tetrahydrofuran was cooled to 10° C., a solution containing 1 g of 2-acetyl-3-t-butyloxycarbonylaminothiophene in 10 ml of tetrahydrofuran was dropwise added at 15° C. or less, and the mixture was stirred at room temperature for 2 hours. Thereafter a saturated aqueous ammonium chloride solution was dropwise added under cooling. The reaction mixture was extracted with ethyl acetate, washed with a saturated aqueous sodium chloride solution and dried over anhydrous sodium solfate. The solvent was distilled off under reduced pressure to obtain 1.2 g of the product. The yield was 98%.

2) 3-amino-2-(1,3-dimethylbutyl)thiophene (Process B)

In 10 ml of methylene chloride, 1.2 g of 2-(1-hydroxy-1,3-dimethylbutyl)-3-t-butoxycarbonylaminothiophene was dissolved, 0.44 g of triethylsilane and 4.3 g of trifluoroacetic acid were added, and the mixture was stirred at the room temperature for 20 hours. The reaction mixture was neutralized with a saturated aqueous sodium hydrogen carbonate solution and extracted with ethyl acetate. The organic layer was washed with a saturated aqueous sodium chloride solution and dried over anhydrous magnesium sulfate. The solvent was distilled off under reduced pressure and the residue was purified by silica gel column chromatography to obtain 0.43 g of the product as a crystal.

3) N-{2-(1,3-dimethylbutyl)-3-thienyl}-3-trifluoromethyl-1-methylpyrazole-4-carboxamide The same procedures as described in Example 3 were carried out except that 3-amino-2-(4-chlorophenyl)thiophene was replaced by 3-amino-2-(1,3-dimethylbutyl)thiophene. The yield was 41%.

Example 15

Preparation of N-(2-isopropyl-3-thienyl)-3-trifluoromethyl-1-methylpyrazole-4-carboxamide
(Compound No. 1.1)

1) 3-amino-2-isopropylthiophene (Process C)

In 10 ml of methylene chloride, 0.9 g of 2-(1-hydroxy-1-methyl) ethyl-3-t-butoxycarbonylaminothiophene (an intermediate in Example 6) was dissolved, 0.41 g of triethylsilane and 4 g of trifluoroacetic acid were added, and the mixture was stirred at the room temperature for 20 hours. Thereafter the reaction mixture was neutralized with a saturated aqueous sodium hydrogen carbonate solution and extracted with ethyl acetate. The ethyl acetate layer was washed with a saturated aqueous sodium chloride solution and dried over anhydrous magnesium sulfate. The solvent was distilled off under reduced pressure and the residue was purified by silica gel column chromatography to obtain 0.29 g of the product as a crystal. The yield was 62%.

2) N-(2-isopropyl-3-thienyl)-3-trifluoromethyl-1-methylpyrazole-4-carboxamide

The same procedures as described in Example 3 were carried out except that 3-amino-2-(4-chlorophenyl)thiophene was replaced by 3-amino-2-isopropylthiophene. The yield was 53%.

Example 16

Preparation of N-(2-isopropyl-3-thienyl)-3-trifluoromethyl-1-methylpyrazole-4-carboxamide
(Compound No. 1.1, Process D)

In 10 ml of methanol, 1 g of the compound prepared in Example 6 (Compound No. 1.71) was dissolved, 0.2 g of 5% Pd/C was added, and catalytic reduction was carried out at the room temperature for 8 hours under atmospheric pressure. After finishing the reaction, the catalyst was filtered and washed with methanol. The filtrate was concentrated under reduced pressure. The resulting oily material was sludged with hexane to obtain 0.8 g of the desired product as a crystal. The yield was 79%.

Other compounds which are represented by the general formula (1) and were prepared by procedures similar to these examples are exemplified in Table 5 to Table 8 below.

TABLE 5

(2-substituted 3-acylamino-thiophene derivatives)

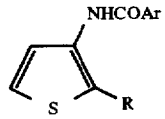

| Compound No. | R | Ar (substituent) | m.p. (°C.) | $^1$H-NMR (400MHz) (CDCl$_3$, δ-value) |
|---|---|---|---|---|
| 1.1 | isopropyl | A2(R$^1$ = CF$_3$) | 109–110 | 1.31(6H, d, J=7.3, 3.20(1H, sept, J=7.3), 3.99(3H, s), 7.11(1H, d, J=5.1), 7.47(1H, d, J=5.1), 7.56(1H, bs), 8.06(1H, s) |
| 1.2 | (1S)-1-methylpropyl | A2(R$^1$ = CF$_3$) | 139–140 | 0.89(3H, t, J=7.3), 1.30(3H, d, J=7.3), 1.59–1.69(2H, m), 2.85–2.93(1H, m), 3.99(3H, s), 7.13(1H, d, J=5.1), 7.46(1H, d, J=5.1), 7.54(1H, bs), 8.05(1H, s) |
| 1.3 | 1-methylpropyl | A1(R$^1$ = CF$_3$, R$^2$ = Me) | | |
| 1.4 | 1-methylpropyl | A2(R$^1$ = CF$_3$) | 112–114 | 0.89(3H, t, J=7.3), 1.30(3H, d, J=7.3), 1.59–1.69(2H, m), 2.85–2.93(1H, m), 3.99(3H, s), 7.13(1H, d, J=5.1), 7.46(1H, d, J=5.1), 7.54(1H, bs), 8.05(1H, s) |
| 1.5 | (1S)-1-methylpropyl | A6 | 96–100 | 0.92(3H, t, J=7.3), 1.33(3H, t, J=7.3), 1.61–1.73(2H, m), 3.30(1H, sext, J=7.3), 7.17(1H, d, J=5.9), 7.42(1H, dd, J=8.1, 5.1), 7.50(1H, d, J=5.9), 8.14(1H, bs), 8.30(1H, dd, J=8.1, 1.5), 8.51(1H, dd, J=5.1, 1.5) |
| 1.6 | 1-ethylpropyl | A2(R$^1$ = CF$_3$) | 126–127 | 0.85(6H, t, J=7.3), 1.49–1.3(2H, m), 1.71–1.81(2H, m), 2.17–2.67(1H, m), 3.99(3H, s), 7.16(1H, d, J=5.9), 7.49(1H, d, J=5.9), 7.55(1H, bs), 8.05(1H, s) |
| 1.7 | 1-methylbutyl | A1(R$^1$ = CF$_3$, R$^2$ = Me) | | |
| 1.8 | 1-methylbutyl | A2(R$^1$ = CF$_3$) | 79–80 | 0.88(3H, t, J=7.3), 1.23–1.8(5H, m), 1.55–1.63(2H, m), 2.98(1H, sext, J=7.3), 3.99(3H, s), 7,13(1H, d, J=5.9), 7.45(1H, d, J=5.9), 7.55(1H, bs), 8.05(1H, s) |
| 1.9 | 1-methylbutyl | A7 | | |
| 1.10 | 1,3-dimethylbutyl | A1(R$^1$ = CF$_3$, R$^2$ = Me) | oil | 0.88(6H, d, J=6.6), 1.27(3H, d, J=6.6), 1.43–1.58(3H, m), 2.77(3H, s), 3.06(1H, m), 7.15(1H, d, J=5.9), 7.41(1H, d, J=5.1), 7.58(1H, brs) |
| 1.11 | 1,3-dimethylbutyl | A1(R$^1$ = CF$_3$, R$^2$ = H) | | |
| 1.12 | 1,3-dimethylbutyl | A1(R$^1$ = R$^2$ = Me) | | |
| 1.13 | 1,3-dimethylbutyl | A2(R$^1$ = CF$_3$) | 103–105 | 0.86(6H, d, J=6.8), 1.25(3H, d, J=6.8), 1.43–1.64(3H, m), 3.08(1H, sext, J=6.8), 3.99(3H, s), 7.12(1H, d, J=5.1), 7.43(1H, d, J=5.1), 7.53(1H, bs), 8.05(1H, s) |
| 1.14 | 1,3-dimethylbutyl | A2(R$^1$ = Me) | | |
| 1.15 | 1,3-dimethylbutyl | A2(R$^1$ = CHF$_2$ | | |

TABLE 5-continued (2-substituted 3-acylamino-thiophene derivatives)

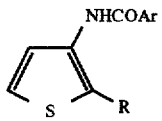

| Compound No. | R | Ar (substituent) | m.p. (°C.) | ¹H-NMR (400MHz) (CDCl₃, δ-value) |
|---|---|---|---|---|
| 1.16 | 1,3-dimethylbutyl | A3($R^1$ = Me, $R^2$ = H) | | |
| 1.17 | 1,2-dimethylbutyl | A3($R^1$ = $R^2$ = Me) | | |
| 1.18 | 1,3-dimethylbutyl | A4($R^1$ = Me, n = 0) | | |
| 1.19 | 1,3-dimethylbutyl | A4($R^1$ = Cl, n = 0) | | |
| 1.20 | 1,3-dimethylbutyl | A5($R^1$ = Me) | | |
| 1.21 | 1,3-dimethylbutyl | A5($R^1$ = Cl) | oil | 0.87(3H, d, J=6.6), 0.88(3H, d, J=6.6), 1.28(3H, d, J=6.6), 1.43–1.65(3H, m), 3.16(1H, sext, J=6.6), 7.15 (1H, d, J=5.1), 7.36–7.52(4H, m), 7.7(1H, brs), 7.83–7.86(1H, m) |
| 1.22 | 1,2-dimethylbutyl | A5($R^1$ = Cl) | | |
| 1.23 | 1,3-dimethylbutyl | A6 | 78.8–83.3 | 0.88(6H, d, J=5.1), 1.30(3H, d, J=6.6), 1.45–1.55(3H, m), 3.17(1H, m), 7.17(1H, d, J=5.1), 7.41–7.45(1H, m), 7.47(1H, d, J=5.1), 8.10(1H, brs), 8.30(1H, d, J=7.3), 8.52(1H, d, J=5.1) |
| 1.24 | 1,2-dimethylbutyl | A2($R^1$ = CF₃) | 100–103 | 0.81–0.92(6H, m), 1.03–1.3(1H, m), 1.27(3H, t, J=6.6), 1.32–1.64(2H, m), 2.84(1H, quint, J=6.6), 3.99(3H, s), 7.14(1H, d, J=5.1), 7.42(1H, d, J=5.1), 7.53(1H, bs), 8.05(1H, s) |
| 1.25 | 1,3-dimethylbutyl | A7 | | |
| 1.26 | tert-butyl | A2($R^1$ = CF₃) | | |
| 1.27 | 1,3-dimethylpentyl | A2($R^1$ = CF₃) | | |
| 1.28 | 1,2-dimethylhexyl | A1($R^1$ = CF₃, $R^2$ = Me) | | |
| 1.29 | 3-methylbutyl | A2($R^1$ = CF₃) | | |
| 1.30 | 3-methylpentyl | A7 | | |
| 1.31 | 1,3-dimethyldecyl | A2($R^1$ = CF₃) | | |
| 1.32 | 1,2,2,3-tetramethylbutyl | A2($R^1$ = CF₃) | | |
| 1.33 | 1,3,3-trimethylbutyl | A2($R^1$ = CF₃) | 150—152 | 0.84(9H, s), 1.26(3H, d, J=6.6), 1.56(2H, m), 3.08(1H, m), 3.99(3H, s), 7.10(1H, d, J=5.7), 7.37(1H, d, J=5.7), 7.53(1H, brs), 8.06(1H, s) |
| 1.34 | 1,3,3-trimethylbutyl | A6 | | |
| 1.35 | 1,2,3-trimethylbutyl | A2($R^1$ = CF₃) | | |
| 1.36 | 1,3-dimethylpentyl | A2($R^1$ = CF₃) | 96–98 | 0.81–0.86(6H, m), 1.21–1.7(8H, m), 3.05(1H, m), 3.99 (3H, s), 7.13(1H, d, J=5.2), 7.42(1H, d, J=5.2), 7.53 (1H, brs), 8.05(1H, s) |
| 1.37 | 1,3-dimethylhexyl | A6 | | |
| 1.38 | 5-methyl-3-hexyl | A2($R^1$ = CF₃) | | |
| 1.39 | 2-methyl-4-heptyl | A2($R^1$ = CF₃) | | |
| 1.40 | 2,6-dimethyl-4-heptyl | A6 | | |
| 1.41 | 1-methyl-2-cyclopropylethyl | A2($R^1$ = CF₃) | 119–123 | 1.18(3H, d, J=7.6), 1.59–2.13(6H, m), 2.41–2.50(1H, m) 2.85–3.02(1H, m), 3.99(3H, s), 7.12(1H, d, J=5.2), 7.45(1H, d, J=5.2), 7.57(1H, bs), 8.06(1H, s) |
| 1.42 | 3-chloro-1-methylbutyl | A2($R^1$ = CF₃) | | |
| 1.43 | 2-chloro-1-methylbutyl | A2($R^1$ = CF₃) | | |
| 1.44 | 1-chlorobutyl | A6 | | |
| 1.45 | 3,3-dichloro-1-methyl | A7 | | |
| 1.46 | 3-chloro-1-methylbutyl | A2($R^1$ = CF₃) | | |
| 1.47 | 3-methyl-1-trifluoromethylbutyl | A2($R^1$ = CF₃) | | |
| 1.48 | 3-methyl-1-trifluoromethylbutyl | A2($R^1$ = CF₃) | | |
| 1.49 | 1,2-dimethylbutyl | A3($R^1$ = Me, $R^2$ = H) | | |
| 1.50 | 1,2-dimethylbutyl | A4($R^1$ = Me, n = 1) | | |
| 1.51 | 1,2-dimethylbutyl | A5($R^1$ = Me) | | |
| 1.52 | 1,3-dimethylpentyl | A1($R^1$ = CF₃, $R^2$ = Me) | | |
| 1.53 | 1,3-dimethylhexyl | A2($R^1$ = CF₃) | | |
| 1.54 | 3-chloro-1-methylbutyl | A1($R^1$ = CF₃, $R^2$ = Me) | | |
| 1.55 | 1-chloro-3-methylbutyl | A2($R^1$ = CF₃) | | |
| 1.56 | cyclohexyl | A2($R^1$ = CF₃) | | |
| 1.57 | 1,3-dimethylbutyl | A2($R^1$ = CF₃) | | |
| 1.58 | 1-methylpropyl | A8($R^1$ = Me) | | |
| 1.59 | 1,3-dimethylbutyl | A8($R^1$ = Me) | | |
| 1.60 | phenyl | A2($R^1$ = CF₃) | 142–144 | 3.96(3H, s), 7.30(1H, d, J=5.1), 7.33–7.46(5H, m), 7.85 (1H, d, J=5.1), 7.87(1H, s), 7.95(1H, brs) |
| 1.61 | 4-chlorophenyl | A2($R^1$ = CF₃) | 149–150 | 3.97(3H, s), 7.31(1H, d, J=5.9), 7.36–7.44(4H, m), 7.77 (1H, brs), 7.80(1H, d, J=5.9), 7.97(1H, s) |
| 1.62 | phenyl | A1($R^1$ = CF₃) | 105–108 | 2.73(3H, s), 7.33(1H, d, J=5.1), 7.37–7.50(5H, m), 7.87 (1H, d, J=5.1), 7.94(1H, brs) |
| 1.63 | 4-chlorophenyl | A5($R^1$ = CF₃) | | |

TABLE 5-continued (2-substituted 3-acylamino-thiophene derivatives)

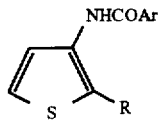

| Compound No. | R | Ar (substituent) | m.p. (°C.) | $^1$H-NMR (400MHz) (CDCl$_3$, δ-value) |
|---|---|---|---|---|
| 1.64 | 4-methoxyphenyl | A2($R^1$ = CF$_3$) | 140–142 | 3.85(3H, s), 3.96(3H, s), 6.97(2H, d, J=8.8), 7.25(1H, d, J=5.1), 7.36(2H, d, J=8.8), 7.80–7.83(2H, m), 7.95 (1H, s) |
| 1.65 | 4-chlorophenyl | A1($R^1$ = CF$_3$, $R^2$ = Me) | 135–137 | 2.74(3H, s), 7.33(1H, d, J=5.1), 7.38(2H, d, J=8.8), 7.43(2H, d, J=8.8), 7.82(1H, d, J=5.1), 7.83(1H, bs) |
| 1.66 | 4-chlorophenyl | A3($R^1$ = $R^2$ = Me) | | |
| 1.67 | 4-chlorophenyl | A4($R^1$ = Me, n = 0) | 108–110 | 2.49(3H, s), 6.91(1H, d, J=5.1), 7.3(1H, d, J=5.2) 7.32(1H, d, J=5.2), 7.44(4H, s), 7.70, 1H, bs), 7.85(1H, d, J=5.1) |
| 1.68 | 4-tolyl | A2($R^1$ = CF$_3$) | 144–146 | 2.39(3H, s), 3.96(3H, s), 7.23–7.35(5H, m), 7.83–7.85 (2H, m), 7.94(1H, s) |
| 1.69 | 4-chlorophenyl | A6 | 133–136 | 7.22–7.46(6H, m), 7.89(1H d, J=5.1), 8.23(1H, dd, J= 1.5, 8.1), 8.37–8.50(2H, m) |
| 1.70 | 4-chlorophenyl | A7 | | |
| 1.71 | isopropenyl | A2($R^1$ = CF$_3$) | 99–104 | 2.12(3H, s), 3.99(3H, s), 5.18(1H, s), 5.33(1H, s), 7.21 (1H, d, J=5.1), 7.78(1H, d, J=5.1), 7.99(1H, s), 8.01 (1H, brs) |
| 1.72 | 1-methylthiopropyl | A2($R^1$ = CF$_3$) | | |
| 1.73 | 1-methylthiopropyl | A1($R^1$ = CF$_3$, $R^2$ = Me) | | |
| 1.74 | 1-methylthioethyl | A1($R^1$ = CF$_3$, $R^2$ = Me) | | |
| 1.75 | 3-chlorophenyl | A2($R^1$ = CF$_3$) | 134–135 | 3.98(3H, s), 7.32–742(4H, m), 7.45(1H, s), 7.82(1H, brs), 7.83(1H, d, J=5.7), 7.99(1H, s) |
| 1.76 | 4-trifluoromethylphenyl | A1($R^1$ = CF$_3$, $R^2$ = Me) | 157–158 | 2.75(3H, s), 7.39(1H, d, J=5.9), 7.57(2H, d, J=8.1), 7.72(2H, d, J=8.1), 7.82–7.84(2H, m) |
| 1.77 | 4-trifluoromethylphenyl | A2($R^1$ = CF$_3$) | 137–138 | 4.03(3H, s), 7.37(1H, d, J=5.1), 7.58(2H, d, J=8.1), 7.70(2H, d, J=8.1), 7.78(1H, brs), 7.81(1H, d, J=5.1), 7.99(1H, s) |
| 1.78 | 4-t-butylphenyl | A2($R^1$ = CF$_3$) | 181–183 | 1.35(9H, s), 3.96(3H, s), 7.27(1H, d, J=5.9), 7.36–7.42 (2H, m), 7.44–7.48(2H, m)7.84–7.86(2H, m), 7.95(1H, s) |
| 1.79 | 4-ethylphenyl | A2($R^1$ = CF$_3$) | 127–129 | 1.26(3H, t, J=7.4), 2.68(2H, q, J=7.4), 3.96(3H, s), 7.29(2H, d, J=8.0), 7.35(2H, d, J=8.0), 7.37(1H, d, J=5.2), 7.83(1H, bs), 7.85(1H, d, J=5.2), 7.95(1H, s) |
| 1.80 | 4-bromophenyl | A2($R^1$ = CF$_3$) | 152–153 | 3.98(3H, s), 7.30–7.35(3H, m), 7.57(2H, d, J=8.8), 7.76 (1H, bs), 7.79(1H, d, J=5.1), 7.97(1H, s) |
| 1.81 | 4-iodophenyl | A2($R^1$ = CF$_3$) | 101–107 | 3.97(3H, s), 7.29–7.34(3H, m), 7.55–7.62(2H, m), 7.76 (1H, bs), 7.79(1H, d, J=5.1), 7.97(1H, s) |
| 1.82 | 4-trifluoromethoxyphenyl | A2($R^1$ = CF$_3$) | 125–127 | 3.96(3H, s), 7.31(2H, d, J=8.8), 7.34(1H, d, J=5.9), 7.48(2H, d, J=8.8), 7.75(1H, bs), 7.80(1H, d, J=5.9), 7.99(1H, s) |
| 1.83 | 4-methylthiophenyl | A2($R^1$ = CF$_3$) | 154–155 | 2.52(3H, s), 3.97(3H, 2), 7.25–7.39(5H, m), 7.80–7.82 (2H, m), 7.95(1H, s) |
| 1.84 | 4-cyclopropylphenyl | A2($R^1$ = CF$_3$) | | |
| 1.85 | 4-methylethynylphenyl | A2($R^1$ = CF$_3$) | | |
| 1.86 | 4-methylsulfinylphenyl | A2($R^1$ = CF$_3$) | | |
| 1.87 | 4-methylsulfonylphenyl | A2($R^1$ = CF$_3$) | 237–238 | 3.09(3H, s), 3.99(3H, s), 7.41(1H, d, J=5.1), 7.67(2H, d, J=8.1), 7.76(1H, brs), 7.78(1H, d, J=5.1), 7.98(1H, s)7.99(2H, d, J=8.1) |
| 1.88 | 3-cyanophenyl | A2($R^1$ = CF$_3$) | | |
| 1.89 | 4-acetylphenyl | A1($R^1$ = CR$_3$, $R^2$ = Me) | | |
| 1.90 | 4-ethoxycarbonylphenyl | A2($R^1$ = CR$_3$) | | |
| 1.91 | 3-aminophenyl | A1($R^1$ = CF$_3$, $R^2$ = Me) | | |
| 1.92 | 4-dimethylaminophenyl | A2($R^1$ = CF$_3$) | | |
| 1.93 | 4-chlorophenyl | A1($R^1$ = CHF$_2$, $R^2$ = Me) | | |
| 1.94 | 4-chlorophenyl | A1($R^1$ = CHF$_2$, $R^2$ = H) | | |
| 1.95 | 4-chlorophenyl | A1($R^1$ = CF$_3$, $R^2$ = H) | | |
| 1.96 | phenyl | A5($R^1$ = Cl) | 118–119 | 7.35–7.53(9H, m), 7.74–7.78(1H, m), 7.99(1H, d, J=5.1) 8.13(1H, brs) |
| 1.97 | phenyl | A6 | 167–170 | 7.35–7.54(7H, m), 7.97(1H, d, J=5.1), 8.23(1H, dd, J= 7.3, 2.2), 8.45(1H, brs), 8.48(1H, dd, J=4.4, 2.2) |
| 1.98 | 1-ethyl-1-phenyl | A2($R^1$ = CF$_3$) | semi-solid | 0.97(3H, t, J=7.3), 1.82(3H, d, J=7.3), 2.39(2H, q, J=7.3), 3.98(3H, s), 5.66(1H, q, J=7.3), 7.17(1H, d, J=5.9), 7.86(1H, d, J=5.9), 8.04(1H, brs), 8.05(1H, s) |
| 1.99 | 1-ethylthioethyl | A2($R^1$ = CF$_3$) | | |
| 1.100 | 3-chlorophnyl | A1($R^1$ = CHF$_2$, $R^2$ = Me) | | |
| 1.101 | 3-chlorophenyl | A3($R^1$ = Me, $R^2$ = H) | | |
| 1.102 | 3-chlorophenyl | A4($R^1$ = Me, n = 0) | | |
| 1.103 | 3-chlorophenyl | A5($R^1$ = Me) | | |
| 1.104 | 3-chlorophenyl | A6 | | |

TABLE 5-continued (2-substituted 3-acylamino-thiophene derivatives)

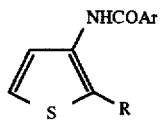

| Compound No. | R | Ar (substituent) | m.p. (°C.) | ¹H-NMR (400MHz) (CDCl₃, δ-value) |
|---|---|---|---|---|
| 1.105 | 3-chlorophenyl | A7 | | |
| 1.106 | 3-tolyl | A2($R^1$ = $CF_3$) | 98–101 | 2.38(3H, s), 3.96(3H, s), 7.18–7.36(5H, m), 7.86–7.88 (2H, m), 7.96(1H, s) |
| 1.107 | 3-tolyl | A1($R^1$ = $CHF_2$, $R^2$ = Me) | | |
| 1.108 | 3-tolyl | A3($R^1$ = $R^2$ = Me) | | |
| 1.109 | 3-tolyl | A4($R^1$ = Me, n = 0) | | |
| 1.110 | 3-tolyl | A5($R^1$ = Cl) | | |
| 1.111 | 3-tolyl | A6 | | |
| 1.112 | 3-tolyl | A7 | | |
| 1.113 | 2-chlorophenyl | A2($R^1$ = $CF_3$) | 110–111 | 3.95(3H, s), 7.32–7.49(4H, m), 7.52(1H, d, J=7.3), 7.58 (1H, brs), 7.88(1H, d, J=5.1), 7.95(1H, s) |
| 1.114 | 2-chlorophenyl | A1($R^1$ = $CF_3$, $R^2$ = Me) | | |
| 1.115 | 3-chlorophenyl | A3($R^1$ = Me, $R^2$ = H) | | |
| 1.116 | 2-chlorophenyl | A4($R^1$ = Me, n = 0) | | |
| 1.117 | 4-fluorophenyl | A1($R^1$ = $CF_3$, $R^2$ = Me) | | |
| 1.118 | 4-fluorophenyl | A2($R^1$ = $CF_3$) | 157–158 | 3.97(3H, s), 7.10–7.19(2H, m), 7.30(1H, d, J=5.1), 7.38–7.46(2H, m), 7.76(1H, brs), 7.81(1H, d, J=5.1), 7.98(1H, s) |
| 1.119 | 3-fluorophenyl | A1($R^1$ = $CF_3$, $R^2$ = Me) | | |
| 1.120 | 3-fluorophenyl | A2($R^1$ = $CF_3$) | 122–124 | 3.97(3H, s), 7.05–7.11(1H, m), 7.14–7.19(1H, m), 7.23 (1H, d, J=7.3), 7.33(1H, d, J=5.9), 7.38–7.46(1H, m), 7.83(2H, d, J=5.9), 7.99(1H, s) |
| 1.121 | 2,4-dichlorophenyl | A2($R^1$ = $CF_3$) | 155–157 | 3.95(3H, s), 7.31–7.38(2H, m), 7.40(1H, d, J=5.9), 7.52–7.55(2H, m), 7.83(1H, d, J=5.9), 7.95(1H, s) |
| 1.122 | 2-fluorophenyl | A1($R^1$ = $CF_3$, $R^2$ = Me) | | |
| 1.123 | 2-fluorophenyl | A2($R^1$ = $CF_3$) | | |
| 1.124 | 3,4-dichlorophenyl | A1($R^1$ = $CF_3$, $R^2$ = Me) | | |
| 1.125 | 3,4-dichlorophenyl | A2($R^1$ = $CF_3$) | 153–154 | 3.98(3H, s), 7.27–7.35(2H, m), 7.51(1H, d, J=8.1), 7.55 (1H, d, J=1.5), 7.76–7.78(2, m), 7.99(1H, s) |
| 1.126 | 3,5-dichlorophenyl | A1($R^1$ = $CF_3$, $R^2$ = Me) | | |
| 1.127 | 3,5-dichlorophenyl | A2($R^1$ = $CF_3$) | 206–207 | 3.98(3H, s), 7.35–7.38(4H, m), 7.80–7.81(2H, m), 8.01 (1H, s) |
| 1.128 | 3,4-difluorophenyl | A2($R^1$ = $CF_3$) | 136–139 | 3.98(3H, s), 7.16–7.29(3H, m), 7.32(1H, d, J=5.1), 7.74 (1H, bs), 7.79(1H, d, J=5.1), 8.00(1H, s) |
| 1.129 | 3,5-difluorophenyl | A2($R^1$ = $CF_3$) | | |
| 1.130 | 3,4-dimethylphenyl | A1($R^1$ = $CF_3$, $R^2$ = Me) | | |
| 1.131 | 3,5-dimethylphenyl | A1($R^1$ = $CF_3$, $R^2$ = Me) | | |
| 1.132 | 3,5-dimethyphenyl | A2($R^1$ = $CF_3$) | 140–141 | 2.34(6H, s), 3.96(3H, s), 7.02(1H, s), 7.06(2H, s), 7.27 (1H, d, J=5.1), 7.87(1H, d, J=5.1), 7.95(1H, brs), 7.96 (1H, s) |
| 1.133 | 3-trifluoromethylphenyl | A2($R^1$ = $CF_3$) | | |
| 1.134 | 3-bromophenyl | A2($R^1$ = $CF_3$) | | |
| 1.135 | 3-iodophenyl | A2($R^1$ = $CF_3$) | | |
| 1.136 | 4-trifluoromethylthiophenyl | A2($R^1$ = $CF_3$) | | |
| 1.137 | 4-cyclopropylphenyl | A2($R^1$ = $CF_3$) | | |
| 1.138 | 4-ethynylphenyl | A2($R^1$ = $CF_3$) | semi-solid | 2.17(1H, s), 3.97(3H, s), 7.29(2H, d, J=8.1), 7.31(1H, d, J=5.1), 7.56(2H, d, J=8.1), 7.64(1H, brs), 7.79(1H, d, J=5.1), 7.97(1H, s) |
| 1.139 | 4-methylsulfinylphenyl | A2($R^1$ = $CF_3$) | | |
| 1.140 | 4-trfluoromethylsufonylphenyl | A2($R^1$ = $CF_3$) | | |
| 1.141 | 3,4,5-trichlorophenyl | A2($R^1$ = $CF_3$) | | |
| 1.142 | 2-tolyl | A2($R^1$ = $CF_3$) | 127–129 | |
| 1.143 | 3-fluoro-4-methylphenyl | A2($R^1$ = $CF_3$) | 98–101 | |
| 1.144 | 4-fluoro-3-methyl-phenyl | A2($R^1$ = $CF_3$) | 142–144 | |
| 1.145 | 4-chloro-3-trifluoromethylphenyl | A2($R^1$ = $CF_3$) | 180–182 | |
| 1.146 | 4-chloro-3-fluorophenyl | A2($R^1$ = $CF_3$) | 126–128 | |
| 1.147 | 3-chloro-4-fluorophenyl | A2($R^1$ = $CF_3$) | 149–150 | |
| 1.148 | 4-chloro-3-methylphenyl | A2($R^1$ = $CF_3$) | 122–124 | |
| 1.149 | 2-isopropylphenyl | A2($R^1$ = $CF_3$) | 110–112 | |
| 1.150 | 3-trfluoromethoxyphenyl | A2($R^1$ = $CF_3$) | 46–50 | |
| 1.151 | 2,5-dichlorophenyl | A2($R^1$ = $CF_3$) | 128–129 | |
| 1.152 | 2-ethylphenyl | A2($R^1$ = $CF_3$) | 111–113 | |
| 1.153 | 4-chloro-3-trifluoromethylphenyl | A1($R^1$ = $CF_3$, $R^2$ = Me) | 149–151 | |
| 1.154 | 4-trifluoromethylphenyl | A5($R^1$ = Cl) | 180–181 | |
| 1.155 | 4-trifluoromethylphenyl | A6 | 169 | |
| 1.156 | 4-trifluoromethylphenyl | A3($R^1$ = Me, $R^2$ = H) | 157–158 | |
| 1.157 | 4-trifluoromethylphenyl | A4($R^1$ = Me, n = 0) | 125–126 | |

TABLE 5-continued (2-substituted 3-acylamino-thiophene derivatives)

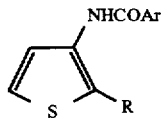

| Compound No. | R | Ar (substituent) | m.p. (°C.) | $^1$H-NMR (400MHz) (CDCl$_3$, δ-value) |
|---|---|---|---|---|
| 1.158 | 3-methoxyphenyl | A2(R$^1$ = CF$_3$) | 109–111 | |
| 1.159 | 4-trifluoromethylphenyl | A8(R$^1$ = Me) | 173–174 | |
| 1.160 | 4-tolyl | A2(R$^1$ = CF$_3$) | 127–129 | |
| 1.161 | 1-methylpentyl | A2(R$^1$ = CF$_3$) | 87–89 | 0.85(3H, m), 1.30(6H, m), 1.58(3H, m), 2.97(1H, m), 3.98 (3H, s), 7.11(1H, d, J=5.2), 7.45(1H, d, J=5.2), 7.54 (1H, brs), 8.05(1H, s) |
| 1.162 | 1-methylhexyl | A2(R$^1$ = CF$_3$) | 90–92 | 0.84(3H, m), 1.23–1.29(11H, m), 2.94(1H, m), 3.99 (3H, s), 7.11(1H, d, J=5.2), 7.45(1H, d, J=5.2), 7.54 (1H, brs), 8.05(1H, s) |
| 1.163 | 1,4-dimethylpentyl | A2(R$^1$ = CF$_3$) | 78–80 | 0.83(6H, d, J=6.6), 1.12–1.64(8H, m), 2.91(1H, m), 3.99 (3H, s), 7.12(1H, d, J=5.1), 7.45(1H, d, J=5.1), 7.55 (1H, brs), 8.05(1H, s) |
| 1.164 | (1S)-1-methylpropyl | A4(R$^1$ = Me, n = 0) | oil | 0.92(3H, t, J=7.3), 1.33(3H, d, J=7.3), 1.66(2H, m), 2.59(3H, s), 2.92(1H, m), 6.95(1H, d, J=5.1), 7.13(1H, d, J=5.9), 7.33(1H, d, J=5.1), 7.45(1H, d, J=5.1) |
| 1.165 | (1S)-1-methylpropyl | A3(R$^1$ = Me, R$^2$ = H) | oil | 0.91(3H, t, J=7.3), 1.31(3H, d, J=6.6), 1.65(2H, m), 2.63(3H, s), 2.91(1H, m), 6.51(1H, brs), 7.12(1H, d, J=5.1), 7.13(1H, brs), 7.30(1H, brs), 7.39(1H, brs) |
| 1.166 | (1S)-1-methylpropyl | A2(R$^1$ = Me) | 82.0–85.5 | 0.91(3H, t, J=7.3), 1.31(3H, d, J=6.6), 1.65(2H, m), 2.54(3H, s), 2.91(1H, m), 3.85(3H, s), 7.12(1H, d, J= 5.9), 7.13(1H, brs), 7.41(1H, brs), 7.76(1H, brs) |
| 1.167 | (1S)-1-methylpropyl | A1(R$^1$ = CF$_3$, R$^2$ = Me) | oil | 0.90(3H, t, J=7.3), 1.31(3H, d, J=6.6), 1.65(2H, m), 2.76(3H, s), 2.88(1H, m), 7.15(1H, d, J=5.1), 7.43(1H, d, J=5.1), 7.64(1H, brs) |
| 1.168 | 1-methylpentyl | A1(R$^1$ = CF$_3$, R$^2$ = Me) | | |
| 1.169 | 1,3-dimethylpentyl | A7 | | |
| 1.170 | 1,3-dimethylpentyl | A5(R$^1$ = Cl) | | |

TABLE 6

(4-substituted acylamino-thiophene derivatives)

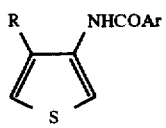

| Compound No. | R | Ar (substituent) | m.p. (°C.) | $^1$H-NMR (400MHz) (CDCl$_3$, δ-value) |
|---|---|---|---|---|
| 2.1 | 1-methylpropyl | A1(R$^1$ = CF$_3$, R$^2$ = Me) | | |
| 2.2 | sec-butyl | A2(R$^1$ = CF$_3$) | | |
| 2.3 | 1,3-dimethylbutyl | A2(R$^1$ = CF$_3$) | | |
| 2.4 | 1,3-dimethylbutyl | A1(R$^1$ = CF$_3$, R$^2$ = Me) | | |
| 2.5 | 1,2-dimethylbutyl | A2(R$^1$ = CF$_3$) | | |
| 2.6 | 1,3-dimethylbutyl | A6 | | |
| 2.7 | 4-tolyl | A1(R$^1$ = CF$_3$, R$^2$ = H) | | |
| 2.8 | 4-tolyl | A2(R$^1$ = CF$_3$) | | |
| 2.9 | 4-chlorophenyl | A2(R$^1$ = CF$_3$) | | |

TABLE 7

(3-substituted 2-acylaminothiophene derivatives)

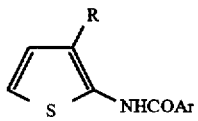

| Compound No. | R | Ar (substituent) | m.p. (°C.) | ¹H-NMR (400MHz) (CDCl₃, δ-value) |
|---|---|---|---|---|
| 3.1 | phenyl | A2($R^1$ = $CF_3$) | 141–142.5 | 3.97(3H, s), 6.97(1H, d, J=5.1), 7.00(1H, d, J=5.1), 7.36–7.52(5H, m), 8.03(1H, s), 8.56(1H, brs) |
| 3.2 | 4-chlorophenyl | A2($R^1$ = $CF_3$) | 166–167 | 3.98(3H, s), 6.93(1H, d, J=5.9), 7.01(1H, d, J=5.9), 7.34(2H, d, J=8.1), 7.45(2H, d, J=8.1), 8.04(1H, s), 8.46((1H, brs) |
| 3.3 | phenyl | A1($R^1$ = $CF_3$, $R^2$ = Me) | oil | 2.74(3H, s), 6.99(1H, d, J=5.1), 7.06(1H, d, J=5.1), 7.36–7.41(3H, m), 7.45–7.52(2H, m), 8.64(1H, brs) |
| 3.4 | 3-chlorophenyl | A3 | | |
| 3.5 | 4-chlorophenyl | A4($R^1$ = Me, n = 0) | | |
| 3.6 | 2-chlorophenyl | A5 | | |
| 3.7 | 3-chlorophenyl | A6 | | |
| 3.8 | 4-chlorophenyl | A7 | | |
| 3.9 | 4-tolyl | A2($R^1$ = $CF_3$) | 153–155 | 2.41(3H, s), 3.96(3H, s), 6.94(1H, d, J=5.9), 6.99(1H, d, J=5.9), 7.29(4H, s), 8.02(1H, s), 8.67(1H, brs) |
| 3.10 | 4-methoxyphenyl | A2($R^1$ = $CF_3$) | 148–151 | 3.87(3H, s), 4.02(3H, s), 6.93(1H, d, J=5.1), 6.98–7.04 (3H, m), 7.32(2H, d, J=8.1), 8.02(1H, s), 8.51(1H, brs) |
| 3.11 | 4-tolyl | A1($R^1$ = $CF_3$, $R^2$ = H) | | |
| 3.12 | 4-methoxyphenyl | A1($R^1$ = $CF_3$, $R^2$ = Me) | 147–148 | 2.74(3H, s), 3.86(3H, s), 9.65(1H, d, J=5.1), 7.00–7.05 (3H, m), 7.32(2H, d, J=8.1), 8.58(1H, brs) |
| 3.13 | phenyl | A6 | 147–151 | |
| 3.14 | phenyl | A5($R^1$ = Cl) | 95–99 | |

TABLE 8

(2-substituted 3-acylaminothiophene derivatives)

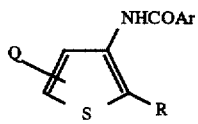

| Compound No. | Q | R | Ar (substituent) | m.p. (°C.) | ¹H-NMR (400MHz) (CDCl₃, δ-value) |
|---|---|---|---|---|---|
| 4.1 | 5-methyl | phenyl | A2($R^1$ = $CF_3$) | 151–152 | |
| 4.2 | 5-methyl | 1,3-dimethylhexyl | A6 | | |
| 4.3 | 5-methoxy | 1,3-dimethylbutyl | A2($R^1$ = $CF_3$) | | |
| 4.4 | 5-methyl | 3-chlorophenyl | A1($R^1$ = $CF_3$, $R^2$ = H) | | |
| 4.5 | 4-chloro | 4-tolyl | A2($R^1$ = $CF_3$) | | |
| 4.6 | 5-methyl | 4-chlorophenyl | A2($R^1$ = $CF_3$) | | |

Next, formulation examples and test examples will be illustrated on the agricultural and horticultural fungicide of the invention.

Formulation Example 1 (Dust Formulation)

100 Parts of dust formulation was prepared by uniformly grinding and mixing 3 parts of the compound having Compound No. 1.2, 20 parts of diatomaceous earth, 77 parts of clay.

Formulation Example 2 (Wettable Powder)

100 Parts of wettable powder was prepared by uniformly grinding and mixing 25 parts of the compound having Compound No. 1.13, 72 parts of diatomaceous earth, 1 part of sodium ligninsulfonate and 2 parts of sodium alkylbenzenesulfonate.

Formulation Example 3 (Wettable Powder)

100 Parts of wettable powder was prepared by uniformly grinding and mixing 50 parts of the compound having Compound No. 1.24, 30 parts of clay, 10 parts of white carbon, 5 parts of sodium laurylphosphate, and 5 parts of sodium alkylnaphthalenesulfonate.

Formulation Example 4 (Wettable Powder)

100 Parts of wettable powder was prepared by uniformly grinding and mixing 50 parts of the compound having Compound No. 1.61, 10 parts of sodium ligninsulfonate, 5 parts of sodium alkylnaphthalenesulfonate, 10 parts of white carbon and 25 parts of diatomaceous earth.

Formulation Example 5 (Emulsifiable Concentrate)

100 Parts of emulsifiable concentrate was prepared by uniformly dissolving and mixing 10 parts of the compound having Compound No. 1.77, 10 parts of cyclohexane, 60 parts of xylene and 20 parts of SORPOL (surface active agent manufactured by Toho Chemical Co.).

Formulation Example 6 (Flowable Formulation)

100 Parts of flowable formulation was prepared by wett-grinding with a sand grinder 40 parts of the compound having Compound No. 1.13, 3 parts of carboxymethylcellulose, 2 parts of sodium ligninsulfonate, 1 part of sodium dioctylsulfosuccinate, and 54 parts of water.

The compounds of the invention will hereinafter be illustrated the activity as an agricultural and horticultural fungicide by way of test examples.

Test Example 1
Control Test (1) Against Gray Mold of Kidney Beans

In a green house, two seedlings of kidney beans (cultivar: Top Crop) were grown in each plastic pot having a diameter of 7.5 cm until development of cotyledon.

A wettable powder which was prepared according to Formulation Example 3 was diluted, to the prescribed concentration (active ingredient concentration of 200 ppm) and air dried after spraying on the seedlings with 50 ml portions per four pots.

A conidiospore suspension ($1\times10^5$ spores/ml) was prepared from gray mold fungus (*Botrytis cinerea*, MBC resistant, RS strain) which was cultured on a PDA medium, and spray-inoculated on the cotyledon, and allowed to stay in a greenhouse at 20°–23° C. for 7 days under relative humidity of 95% or more.

After 7 days from the inoculation, the lesion area of gray mold per leaf of kidney beans was examined on the basis of the following index. Results are illustrated in Table 9. The numerical value in the Table shows a preventive value, and "-" means untested.

Severity
0: no lesion
1: lesion area is 5% or less
2: lesion area is 5–25%
3: lesion area is 25–50%
4: lesion area is 50% or more The mean value of each treated area and untreated area is defined as severity.

Preventive value (%)=(1−severity in the treated area/severity in the untreated area)×100

Test Example 2
Control Test 2) Against Gray Mold of Kidney Beans

In a green house, two seedlings of kidney beans (cultivar: Top Crop) were grown in each plastic pot having a diameter of 7.5 cm until development of cotyledon.

A wettable powder which was prepared according to Formulation Example 3 was diluted to the prescribed concentration (active ingredient concentration of 200 ppm) and air dried after spraying on the seedlings with 50 ml portions per four pots.

A conidiospore suspension ($1\times10^5$ spores/ml) was prepared from gray mold (*Botrytis cinerea*, MBC resistant, dicarboximide resistant, RR strain) which was cultured on a PDA medium, and spray-inoculated on the cotyledon, and allowed to stay in a greenhouse at 20°–23° C. for 7 days under relative humidity of 95% or more.

After 7 days from the inoculation, the lesion area of gray mold per leaf of kidney beans was examined on the basis of the following index. Results are illustrated in Table 9.

Severity
0: no lesion
1: lesion area is 5% or less
2: lesion area is 5–25%
3: lesion area is 25–50%
4: lesion area is 50% or more The mean value of each treated area and untreated area is defined as severity.

Preventive value (%)=(1−severity in the treated area/severity in the untreated area)×100

Test Example 3
Control Test Against Cucumber Powdery Mildew

In a green house, two seedlings of cucumber (cultivar: Sagami Hanjiro) were grown in each plastic pot having a diameter of 7.5 cm until the 1.5 leaf stage.

A wettable powder which was prepared according to Formulation Example 3 was diluted to the prescribed concentration (active ingredient concentration of 200 ppm) and air dried after spraying on the seedlings with 50 ml portions per three pots.

A conidiospore suspension ($1\times10^6$ spores/ml) was prepared by suspending conidiospore of cucumber powdery mildew fungus in water which contains a small amount of spreader, and spray inoculated on the leaf, and allowed to stay in a greenhouse for 7 days.

After 7 days from the inoculation, the lesion area of powdery mildew per leaf of cucumber was examined on the basis of the following index. Results are illustrated in Table 9.

Severity
0: no lesion
1: lesion area is 5% or less
2: lesion area is 5–25%
3: lesion area is 25–50%
4: lesion area is 50% or more The mean value of each treated area and untreated area is defined as severity.

Preventive value (%)=(1−severity in the treated area/severity in the untreated area)×100

Test Example 4
Control Test Against Wheat Powdery Mildew (EBI Resistant Strain)

In a green house, 15–20 seedlings of wheat (cultivar: Chihoku) were grown in each plastic pot having a diameter of 6 cm until the 1.5 leaf stage.

A wettable powder which was prepared according to Formulation Example 3 was diluted to the prescribed concentration (active ingredient concentration of 200 ppm) and air dried after spraying on the seedlings with 50 ml portions per three pots.

Thus treated seedlings were successively sprayed with conidiospore of wheat powdery mildew fungus (*Erysiphe graminis* f. sp. *tritici*, EBI resistant strain) and allowed to stand in a room at 18° C.

After 7 days from the inoculation, the lesion area of powdery mildew on the primary leaf of wheat was examined on the basis of the following index. Results are illustrated in Table 9.

Severity
0: no lesion
1: lesion area is 5% or less
2: lesion area is 5–25%
3: lesion area is 25–50%
4: lesion area is 50% or more The mean value of each treated area and untreated area is defined as severity.

Preventive value (%)=(1−severity in the treated area/severity in the untreated area)×100

Test Example 5
Control Test Against Wheat Brown Rust

In a green house, 15-20 seedlings of wheat (cultivar: Norin NO. 64) were grown in each plastic pot having a diameter of 6 cm until the 1.5 leaf stage.

A wettable powder which was prepared according to Formulation Example 4 was diluted to the prescribed concentration (active ingredient concentration of 200 ppm) and air dried after spraying on the seedlings with 50 ml portions per three pots.

Thus treated seedlings were successively sprayed with summer spore of wheat brown rust fungus (*Puccinia recondita*), allowed to stand in a moist condition for 2 days and transferred to a room which was maintained at 18° C.

After 10 days from the inoculation, the lesion area of red rust on the primary leaf of wheat was examined on the basis of the following index. Results are illustrated in Table 9.

Severity

0: no lesion

1: lesion area is 5% or less

2: lesion area is 5-25%

3: lesion area is 25-50%

4: lesion area is 50% or more

The mean value of each treated area and untreated area is defined as severity.

Preventive value (%)=(1−severity in the treated area/severity in the untreated area)×100

TABLE 9

| Compound No. | Example 1 Gray mold (RS strain) | Example 2 Gray mold (RR strain) | Example 3 Powdery mildew (EBI sensitive) | Example 4 Powdery mildew (EBI resistant) | Example 5 Rust (EBI sensitive) |
|---|---|---|---|---|---|
| 1.1 | 100 | 100 | 100 | 100 | 100 |
| 1.2 | 100 | 100 | 100 | 100 | 100 |
| 1.4 | 100 | 100 | 100 | 100 | 100 |
| 1.5 | 100 | 100 | 100 | 30 | 50 |
| 1.6 | 100 | 100 | 100 | 100 | 100 |
| 1.7 | 100 | 100 | 100 | 100 | 100 |
| 1.8 | 100 | 100 | 100 | 100 | 100 |
| 1.10 | 100 | 100 | 100 | 100 | 100 |
| 1.13 | 100 | 100 | 100 | 100 | 100 |
| 1.21 | 80 | 100 | 100 | 100 | — |
| 1.23 | 100 | 100 | 100 | 100 | 100 |
| 1.24 | 100 | 100 | 100 | 100 | 100 |
| 1.33 | 50 | 45 | 100 | 100 | 100 |
| 1.36 | 100 | 100 | 100 | 100 | 100 |
| 1.41 | 100 | 100 | 100 | 100 | 100 |
| 1.60 | 100 | 100 | 100 | 100 | 83 |
| 1.61 | 100 | 100 | 100 | 100 | 100 |
| 1.62 | 100 | 100 | 100 | 100 | 83 |
| 1.64 | 100 | 100 | 43 | 33 | 45 |
| 1.65 | 100 | 100 | 90 | 83 | 83 |
| 1.67 | 100 | 100 | 100 | 100 | 100 |
| 1.68 | 100 | 100 | 100 | 100 | 47 |
| 1.69 | 100 | 100 | 90 | 90 | 33 |
| 1.71 | 100 | 100 | 40 | 33 | 100 |
| 1.75 | 100 | 100 | 100 | 100 | 100 |
| 1.76 | 90 | 90 | 100 | 100 | 83 |
| 1.77 | 100 | 100 | 100 | 100 | 100 |
| 1.78 | 100 | 100 | 100 | 100 | 90 |
| 1.79 | 100 | 100 | 100 | 100 | 30 |
| 1.80 | 100 | 100 | 100 | 100 | 100 |
| 1.81 | 100 | 100 | 100 | 100 | 100 |
| 1.82 | 100 | 100 | 100 | 100 | 33 |
| 1.83 | 100 | 100 | 30 | 30 | 90 |
| 1.87 | 90 | 90 | 30 | 30 | 33 |
| 1.96 | 80 | 70 | 40 | 40 | 90 |
| 1.97 | 100 | 100 | 40 | 40 | 100 |
| 1.98 | 100 | 100 | 95 | 90 | 100 |

TABLE 9-continued

| Compound No. | Example 1 Gray mold (RS strain) | Example 2 Gray mold (RR strain) | Example 3 Powdery mildew (EBI sensitive) | Example 4 Powdery mildew (EBI resistant) | Example 5 Rust (EBI sensitive) |
|---|---|---|---|---|---|
| 1.106 | 100 | 100 | 100 | 100 | 100 |
| 1.113 | 100 | 100 | 100 | 100 | 100 |
| 1.118 | 100 | 100 | 100 | 100 | 100 |
| 1.120 | 100 | 100 | 100 | 100 | 100 |
| 1.121 | 100 | 100 | 100 | 100 | 100 |
| 1.125 | 100 | 100 | 100 | 100 | 100 |
| 1.127 | 100 | 100 | 100 | 100 | 100 |
| 1.128 | 30 | 25 | 100 | 100 | 80 |
| 1.132 | 30 | 30 | 100 | 100 | 90 |
| 1.138 | 25 | 30 | 100 | 100 | 90 |
| 1.142 | 100 | 100 | 90 | 80 | 100 |
| 1.143 | 100 | 100 | 100 | 100 | 100 |
| 1.144 | 100 | 100 | 100 | 100 | 100 |
| 1.145 | 100 | 100 | 100 | 100 | 100 |
| 1.146 | 100 | 100 | 100 | 100 | 100 |
| 1.147 | 100 | 100 | 100 | 100 | 100 |
| 1.148 | 100 | 100 | 100 | 100 | 100 |
| 1.149 | 100 | 100 | 100 | 100 | 100 |
| 1.150 | 100 | 100 | 100 | 100 | 40 |
| 1.151 | 100 | 100 | 90 | 90 | 100 |
| 1.152 | 100 | 100 | 80 | 80 | 30 |
| 1.153 | 30 | 20 | 100 | 100 | 100 |
| 1.156 | 60 | 70 | 0 | 0 | 0 |
| 1.157 | 70 | 70 | 100 | 100 | 30 |
| 1.158 | 100 | 100 | 100 | 100 | 100 |
| 1.159 | 70 | 60 | 0 | 0 | 0 |
| 1.160 | 100 | 100 | 100 | 100 | 80 |
| 1.161 | 100 | 100 | 100 | 100 | 100 |
| 1.162 | 80 | 70 | 100 | 100 | 100 |
| 1.163 | 80 | 80 | 100 | 100 | 100 |
| 1.164 | 100 | 100 | 100 | 100 | 100 |
| 1.165 | 100 | 100 | 80 | 85 | 100 |
| 1.166 | 80 | 70 | 100 | 100 | — |
| 1.167 | 80 | 75 | 100 | 100 | — |
| 3.1 | 100 | 100 | 70 | 70 | 30 |
| 3.2 | 90 | 90 | 100 | 100 | 90 |
| 3.3 | 100 | 100 | 80 | 70 | 30 |
| 3.9 | 70 | 60 | 0 | 0 | 0 |
| 3.12 | 30 | 20 | 100 | 100 | 90 |
| 3.13 | 100 | 80 | 0 | 0 | 100 |
| 3.14 | 100 | 90 | 0 | 0 | 100 |
| 4.1 | 90 | 80 | 0 | 0 | 0 |
| Ref. Comp No. 1 | 100 | 0 | — | — | — |
| Ref. Comp No. 2 | — | — | 100 | 0 | 87 |
| Ref. Comp No. 3 | 10 | 20 | 0 | 0 | 0 |
| Ref. Comp No. 4 | 30 | 20 | 0 | 0 | 0 |

Reference Compound
No. 1: procymidone; N-(3,5-dichlorophenyl)-1,2-dimethylcyclopropane-1,2-dicarboxamide
No. 2: triadimefon; 1-(4-chlorophenoxy)-3,3-dimethyl-1-(1,2,4-triazol-1-yl)-2-butanone
No. 3: N-(2-isopropylphenyl)-5-chloro-1,3-dimethylpyrazole-4-carboxamide
No. 4: N-(2-propylphenyl)-2-methyl-4-trifluoromethylthiazole-5-carboxamide

What is claimed is:

1. A substituted thiophene compound of the formula (1)

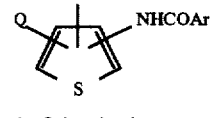

wherein Q is a hydrogen atom, fluorine atom, chlorine atom, bromine atom, iodine atom, methyl group, trifluoromethyl group, methoxy group, methylthio group, methylsulfonyl group, methylsulfoxy group, nitro group or amino group; R is a straight or branched alkyl group having 1–12 carbon atoms, straight or branched halogenalkyl group having 1–12 carbon atoms, straight or branched alkenyl group having 2–10 carbon atoms, straight or branched halogenoalkenyl group having 2–10 carbon atoms, alkoxyalkyl group having 2–10 carbon atoms, alkylthioalkyl group having 2–10 carbon atoms, cycloalkyl group having 3–10 carbon atoms, halogen substituted cycloalkyl group having 3–10 carbon atoms, or a phenyl group which can be substituted with 1–3 substituents; the 1–3 substituents of said phenyl group are selected from a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group or amino group substituted with alkyl group having 1–3 carbon atoms; R and the group —NHCOAr are at adjacent positions on the thiophene ring; and Ar is a group of one of the following formulae (A1) to (A8):

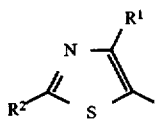 (A1)

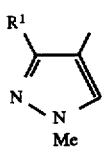 (A2)

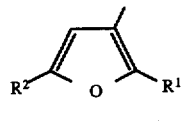 (A3)

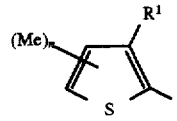 (A4)

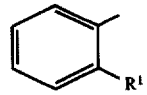 (A5)

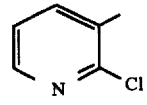 (A6)

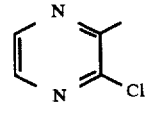 (A7)

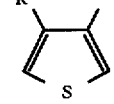 (A8)

wherein $R^1$ is a trifluoromethyl group, difluoromethyl group, methyl group, ethyl group, chlorine atom, bromine atom or iodine atom, $R^2$ is a hydrogen atom, methyl group, trifluoromethyl group or amino group, and n is an integer of 0–2.

2. A substituted thiophene compound according to claim 1 wherein Q is a hydrogen atom, R is a straight or branched alkyl group having 1–12 carbon atoms, straight or branched halogenoalkyl group having 1–12 carbon atoms, or cycloalkyl group having 3–10 carbon atoms.

3. A substituted thiophene compound according to claim 2 wherein Ar is (A2).

4. A substituted thiophene derivative according to claim 3 wherein R is a branched alkyl group having 3–12 carbon atoms.

5. A substituted thiophene compound according to claim 1 wherein Q is a hydrogen atom, R is a phenyl group which can be substituted with 1–3 substituents, and the substituent of said phenyl group is hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group, or amino group substituted with alkyl group having 1–3 carbon atoms.

6. An agricultural and horticultural fungicide comprising, as an active ingredient, a substituted thiophene compound of the formula (1):

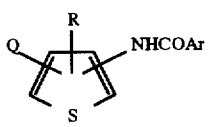 (1)

wherein Q is a hydrogen atom, fluorine atom, chlorine atom, bromine atom, iodine atom, methyl group, trifluoromethyl group, methoxy group, methylthio group, methylsulfonyl group, methylsulfoxy group, nitro group or amino group; R is a straight or branched alkyl group having 1–12 carbon atoms, straight or branched halogenalkyl group having 1–12 carbon atoms, straight or branched alkenyl group having 2–10 carbon atoms, straight or branched halogenoalkenyl group having 2–10 carbon atoms, alkoxyalkyl group having 2–10 carbon atoms, alkylthioalkyl group having 2–10 carbon atoms, cycloalkyl group having 3–10 carbon atoms, halogen substituted cycloalkyl group having 3–10 carbon atoms, or a phenyl group which can be substituted with 1–3 substituents; the 1–3 substituents of said phenyl group a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group or amino group substituted with alkyl group having 1–3 carbon atoms; R and the group —NHCOAr are at adjacent positions on the thiophene ring; and Ar is a group of one of the following formulae (A1) to (A8):

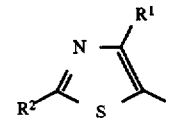 (A1)

-continued

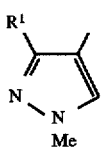

(A2)

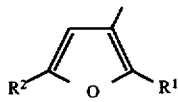

(A3)

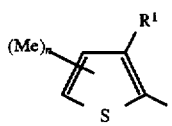

(A4)

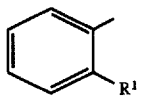

(A5)

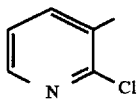

(A6)

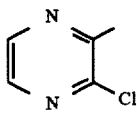

(A7)

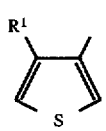

(A8)

wherein $R^1$ is a trifluoromethyl group, difluoromethyl group, methyl group, ethyl group, chlorine atom, bromine atom or iodine atom, $R^2$ is a hydrogen atom, methyl group, trifluoromethyl group or amino group, and n is an integer of 0–2.

7. An agricultural and horticultural fungicide according to claim 6 wherein Q is a hydrogen atom, R is a straight or branched alkyl group having 1–12 carbon atoms, straight or branched halogenoalkyl group having 1–12 carbon atoms, or cycloalkyl group having 3–10 carbon atoms.

8. An agricultural and horticultural fungicide according to claim 7 wherein Ar is (A2).

9. An agricultural and horticultural fungicide according to claim 8 wherein R is a branched alkyl group having 3–12 carbon atoms.

10. An agricultural and horticultural fungicide according to claim 6 wherein Q is hydrogen atom, R is phenyl group which can be substituted with 1–3 substituents, and the substituent of said phenyl group is a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group, or amino group substituted with alkyl group having 1–3 carbon atoms.

11. A method for controlling plant disease comprising applying a substituted thiophene compound of the formula (1):

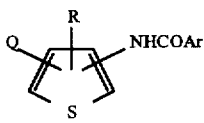

(1)

wherein Q is a hydrogen atom, fluorine atom, chlorine atom, bromine atom, iodine atom, methyl group, trifluoromethyl group, methoxy group, methylthio group, methylsulfonyl group, methylsulfoxy group, nitro group or amino group; R is a straight or branched alkyl group having 1–12 carbon atoms, straight or branched halogenalkyl group having 1–12 carbon atoms, straight or branched alkenyl group having 2–10 carbon atoms, straight or branched halogenoalkenyl group having 2–10 carbon atoms, alkoxyalkyl group having 2–10 carbon atoms, alkylthioalkyl group having 2–10 carbon atoms, cycloalkyl group having 3–10 carbon atoms, halogen substituted cycloalkyl group having 3–10 carbon atoms, or a phenyl group which can be substituted with 1–3 substituents; the 1–3 substituents of said phenyl group are selected from a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group or amino group substituted with alkyl group having 1–3 carbon atoms; R and the group —NHCOAr are at adjacent positions on the thiophene ring; and Ar is a group of one of the following formulae (A1) to (A8):

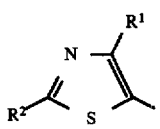

(A1)

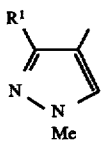

(A2)

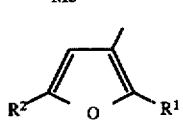

(A3)

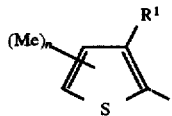

(A4)

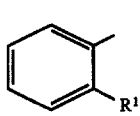

(A5)

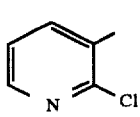

(A6)

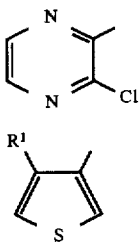 (A7)

(A8)

wherein R¹ is a trifluoromethyl group, difluoromethyl group, methyl group, ethyl group, chlorine atom, bromine atom or iodine atom, R² is a hydrogen atom, methyl group, trifluoromethyl group or amino group, and n is an integer of 0–2.

12. A method for controlling plant disease according to claim 11 wherein Q is a hydrogen atom, R is a straight or branched alkyl group having 1–12 carbon atoms, straight or branched halogenoalkyl group having 1–12 carbon atoms, or cycloalkyl group having 3–10 carbon atoms.

13. A method for controlling plant disease according to claim 12 wherein Ar is (A2).

14. A method for controlling plant disease according to claim 13 wherein R is a branched alkyl group having 3–12 carbon atoms.

15. A method for controlling plant disease according to claim 11 wherein Q is a hydrogen atom, R is a phenyl group which can be substituted with 1–3 substituents, and the substituent of said phenyl group is a hydrogen atom, alkyl group having 1–4 carbon atoms, alkenyl group having 2–4 carbon atoms, alkynyl group having 2–4 carbon atoms, cycloalkyl group having 3–6 carbon atoms, alkoxy group having 1–4 carbon atoms, halogenoalkoxy group having 1–4 carbon atoms, alkylthio group having 1–4 carbon atoms, alkylsulfoxy group having 1–4 carbon atoms, alkylsulfonyl group having 1–4 carbon atoms, halogen atom, cyano group, acyl group having 2–4 carbon atoms, alkoxycarbonyl group having 2–4 carbon atoms, amino group, or amino group substituted with alkyl group having 1–3 carbon atoms.

16. The method of claim 11, wherein the substituted thiophene compound is applied in an amount of 50–1000 g/hectare of the plants for which disease is to be controlled.

17. A substituted thiophene compound of claim 1, which is N-{2-(1,3-dimethylbutyl)-3-thienyl}-3-trifluoromethyl-1-methylpyrazole-4-carboxamide.

* * * * *